US009848771B2

(12) United States Patent
Maddess et al.

(10) Patent No.: US 9,848,771 B2
(45) Date of Patent: Dec. 26, 2017

(54) CLUSTERED VOLLEY METHOD AND APPARATUS

(71) Applicant: The Australian National University, Acton (AU)

(72) Inventors: Teddy Lee Maddess, Lyneham (AU); Andrew Charles James, Griffith (AU); Corinne Frances Carle, Wanniassa (AU)

(73) Assignee: The Australian National University, Acton (AU)

( * ) Notice: Subject to any disclaimer, the term of this patent is extended or adjusted under 35 U.S.C. 154(b) by 169 days.

(21) Appl. No.: 14/441,387

(22) PCT Filed: Nov. 25, 2013

(86) PCT No.: PCT/AU2013/001358
§ 371 (c)(1),
(2) Date: May 7, 2015

(87) PCT Pub. No.: WO2014/078909
PCT Pub. Date: May 30, 2014

(65) Prior Publication Data
US 2015/0282704 A1    Oct. 8, 2015

(30) Foreign Application Priority Data
Nov. 26, 2012 (AU) ................................ 2012905171

(51) Int. Cl.
*A61B 5/00* (2006.01)
*A61B 3/11* (2006.01)
(Continued)

(52) U.S. Cl.
CPC ............ *A61B 3/112* (2013.01); *A61B 3/0025* (2013.01); *A61B 3/0041* (2013.01); *A61B 3/024* (2013.01);
(Continued)

(58) Field of Classification Search
CPC ..... A61B 3/112; A61B 3/0025; A61B 3/0041; A61B 3/0058; A61B 3/02; A61B 3/024; A61B 3/032
See application file for complete search history.

(56) References Cited

U.S. PATENT DOCUMENTS

| 4,846,567 A | 7/1989 | Sutter |
| 5,539,482 A | 7/1996 | James et al. |

(Continued)

FOREIGN PATENT DOCUMENTS

| WO | 2005/051193 A1 | 6/2005 |
| WO | 2010/063064 | 6/2010 |

OTHER PUBLICATIONS

D. Gamlin, "The pretectum: connections and oculomotor-related roles", Prog Brain Res, 2006, vol. 151, pp. 379-405.
(Continued)

*Primary Examiner* — Max Hindenburg
(74) *Attorney, Agent, or Firm* — Wood, Phillips, Katz, Clark & Mortimer

(57) ABSTRACT

Systems and methods are disclosed for assessing the function of parts of one or more sensory fields of a subject. Pupillary responses to at least two clustered ensembles of stimuli presented to predetermined portions of the sensory fields to be tested are measured. Each cluster comprises individual stimuli presented at locations across the sensory field, where the locations are defined on appropriate axes for the tested sensory fields. The method comprises: presenting statistically independent sequences of selected individual stimuli from the two or more clustered stimulus ensembles to a sensory field of a subject, thereby evoking pupillary responses in at least one pupil of the subject; detecting responses of the pupil or pupils evoked by the stimuli using at least one sensor; and processing the detected responses to relate the detected response to the sensory function of each (Continued)

component part of the sensory field. The sensory fields may be, but are not limited to, the visual fields of the two eyes of a subject.

15 Claims, 18 Drawing Sheets

(51) Int. Cl.
*A61B 3/024* (2006.01)
*A61B 3/032* (2006.01)
*A61B 3/00* (2006.01)
*A61B 3/113* (2006.01)
*A61B 3/117* (2006.01)
*A61B 5/11* (2006.01)

(52) U.S. Cl.
CPC .............. *A61B 3/032* (2013.01); *A61B 3/113* (2013.01); *A61B 3/1173* (2013.01); *A61B 5/4005* (2013.01); *A61B 5/1104* (2013.01)

(56) References Cited

U.S. PATENT DOCUMENTS

| | | | |
|---|---|---|---|
| 6,315,414 | B1 | 11/2001 | Maddess et al. |
| 7,006,863 | B2 | 2/2006 | Maddess et al. |
| 8,807,753 | B2 * | 8/2014 | Maddess ................. A61B 5/16 351/209 |
| 8,911,085 | B2 * | 12/2014 | Privitera ................. A61B 3/112 351/200 |
| 9,039,182 | B2 * | 5/2015 | Huang ..................... G06K 9/46 351/239 |
| 2011/0292342 | A1 * | 12/2011 | Maddess ................. A61B 5/40 351/209 |

OTHER PUBLICATIONS

D. M. Dacey, H. W. Lioa, B. B. Peterson, F. R. Robinson, V. C. Smith, J. Pokorny, K. W. Yau and P.D. Gamlin, "Melanopsin-expressing ganglion cells in primate retina signal colour and irradiance and project to the LGN", Nature, 2005, vol. 433, Issue 7027, pp. 749-754.
S. Shipp, "The functional logic of cortico-pulvinar connections", Philos Trans R Soc Long B Biol Sci, Oct. 29, 2003, vol. 358 (1438), pp. 1605-1624.
S. Clarke, S. Riahi-Arya, E. Tardif, A. C. Eskenasy and A. Probst, "Thalamic projections of the fusiform gyrus in man" Eur J Neursci, May 1999, vol. 11 (5), pp. 1835-1838.
F. J. Rucker and P. B. Kruger, "Accommodation responses to stimuli in cone contrast space", Vision Res, Nov. 2004, vol. 44 (25), pp. 2931-2944.
J. Slooter and D. van Norren, "Visual acuity measured with pupil responses to checkerboard stimuli", Invest Opthalmol Vis Sci, Jan. 1980, vol. 19 (1), pp. 105-108.
K. D. Cocker and M. J. Mosely, "Development of pupillary responses to grating stimuli", Ophthalmic Physiol Opt, Jan. 1996, vol. 16 (1), pp. 64-67.
E. A. Benardet, E. Kaplan and B. W. Knight, "Contrast gain control in the primate retina: P. cells are not X-like, some M cells are", Vis Neurosci, May 1992, vol. 8 (5), pp. 483-486.

* cited by examiner

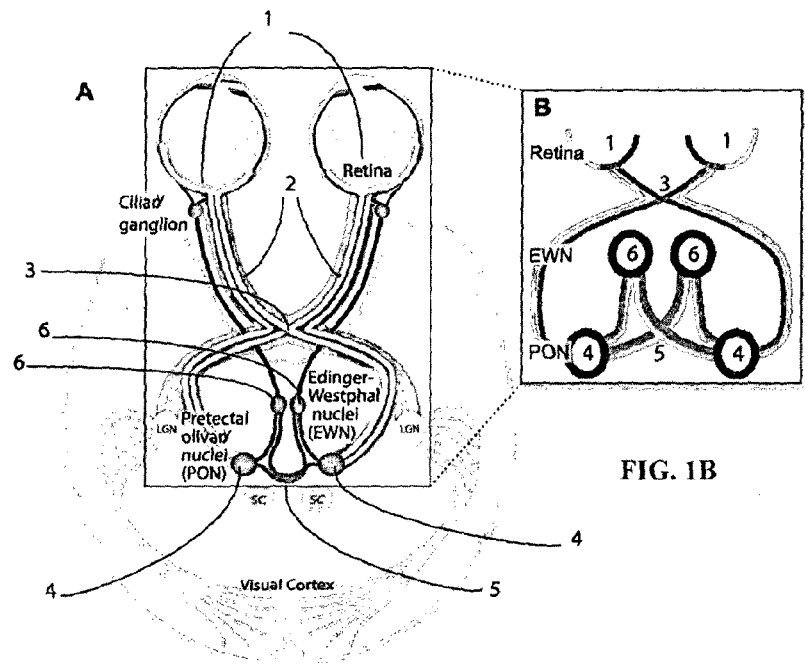
FIG. 1A
FIG. 1B
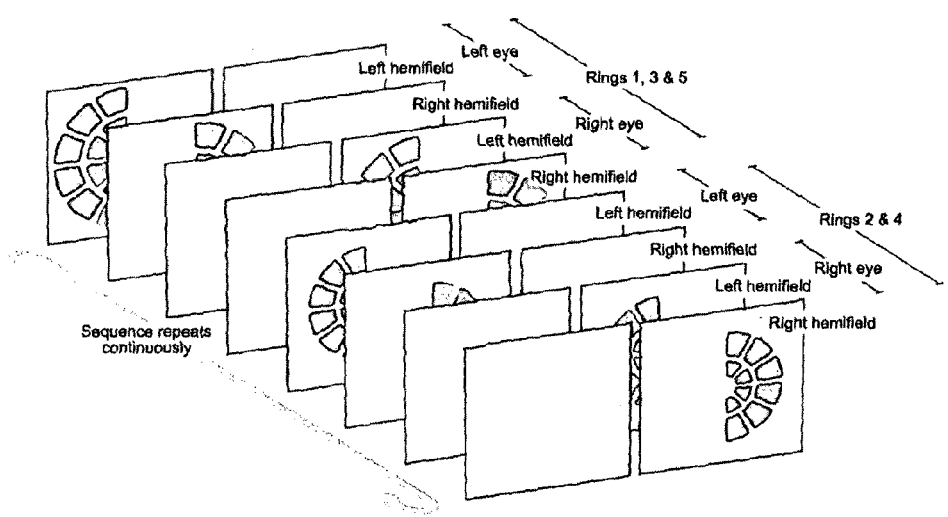
FIG. 4

CLUSTERED VOLLEY METHOD AND APPARATUS

RELATED APPLICATION

The present application claims the benefit of the earlier filing date of Australian Provisional Patent Application No. 2012905171 filed on 26 Nov. 2012 of the same title, which is incorporated by reference herein in its entirety.

TECHNICAL FIELD

The present invention relates generally to method and systems for assessing the function of the nervous system using the pupil and the pupil's unique properties and in particular to methods and systems for assessing the operation of the visual sensory system.

BACKGROUND

Any discussion of the background art throughout the specification should in no way be considered as an admission that such background art is prior art, nor that such background art is widely known or forms part of the common general knowledge in the field.

In the human, each optic nerve contains about 1,000,000 nerve fibres, which convey information from all parts of each retina to the brain. A fundamental design feature of the human visual system is the chiasm, which allows visual information from the left half of each retina, to proceed to the right half of the brain and from the right half of each retina to go to the left half of the brain. Each half of the retina corresponds to half the visual field, a so called hemifield. This arrangement allows each of the left and right halves of the visual brain to receive binocular information about a half of the visual field. Subsequent communication between the two halves of the brain, such as via the corpus callosum, allows the two halves of the visual field to be perceived as a whole.

The pupils of eyes have more functions than being a camera aperture that regulates the flux of light into the eye via a simple reflex mediated by parts of the midbrain. The added sophistication of pupillary function is in part derived from the inputs from various brain areas that contribute to the pupillary response including higher brain areas of the visual cortex. These many individual responses must be combined, or pooled, in some way in order to cause the pupils to respond to visual stimuli. FIG. 1A illustrates the afferent pathways (including optical nerves 2) from the two eyes 1 via the chiasm 3 to two pretectal olivary nuclei (PONs) 4, and then the efferent portion via a second chiasm to two Edinger-Westphal nuclei (EWN) 6 and then onto the cilary ganglia, and FIG. 1B at right shows a simplified version of these pathways.

The first site of combination of many component signals to give a single observed pupil response is the pretectal olivary nucleus (PON) 4. There is one PON on each side of the head, and each receives information from half of each of the two retinas 1. The two PONs 4 then convey information to both of the Edinger-Westphal (EW) nuclei 6, one on each side of the brain, which in turn innervate the pupils via the oculomotor nerves. This represents a so-called second decussation, that is to say a second chiasm. This circuitry means that each pupil receives information about the pooled activity of both retinas 1, and importantly, that either pupil can respond to stimulation to the left or right half of the visual field of either eye. Thus each pupil can independently provide information on the operation of both retinas 1. When a pupil gives a response to the retina of its own eye this is said to be a direct response. When a pupil responds to activity from the retina of its fellow eye that is said to be a consensual response. Importantly, at each stage of pooling, in the PON 4 or the EWN 6, there is the opportunity for visual processing, that may include gain control. Thus, in the pupil system, gain control may be separately controlled for each half retina or each half of the visual field.

About half the input to the PON is from melanopsin containing retinal ganglion cells (mcRGC) that come directly from the eye [for further information see P. D. Gamlin, "The pretectum: connections and oculomotor-related roles", *Prog Brain Res*, 2006, Volume 151, Pages 379-405]. That work also describes the connectivity of the PON in detail. The nerve fibres of these and all the other types of retinal ganglion cells make up the optic nerve projecting from the eye to the brain. These mcRGCs are the neurons running from the eye to the PON illustrated in FIG. 1A. The mcRGCs have two separate types of responses to light [for further information see D. M. Dacey, H. W. Liao, B. B. Peterson, F. R. Robinson, V. C. Smith, J. Pokorny, K. W. Yau and P. D. Gamlin, "Melanopsin-expressing ganglion cells in primate retina signal colour and irradiance and project to the LGN", *Nature*, 2005, Volume 433, Issue 7027, Pages 749-754]. The first response type derives from melanopsin that is present in the cell bodies and dendritic arms of these ganglion cells in the retina. Unlike the light responses of the photoreceptor cells of the retina the melanposin driven response of mcRGCs has no light adaptation mechanism and so increases steadily with increasing light level. The melanopsin pigment responds to blue light and the response itself is very slow, taking several seconds to respond to a transient increase in blue light. This slow integrative response is mainly responsible for the mean pupil size, smaller in bright light, more dilated in dim light.

As with all other types of retinal ganglion cells (RGCs), the mcRGCs also convey signals derived from rod and cone photoreceptor cells of the eye. The cone driven component responds positively to yellow light (luminance) and negatively to blue light. This response type is often referred to as a Yellow-ON/Blue-OFF class of response. These responses are much more transient maintaining the time resolution of the cones. This system also necessarily embodies the light adaptation mechanism possessed by the photoreceptors and cells that process photoreceptor information such as bipolar and horizontal cells before those signals are passed to the RGCs. Other types of retinal ganglion cells convey information to the brain about differential red and green content of images, and also, the luminance (brightness) information in images. The main luminance signals are conveyed to the brain by the parasol retinal ganglion cells. The red-green colour signal is carried by midget retinal ganglion cells. Together the parasol and midget cells make up the majority of the optic nerve fibres in humans and allied primates.

Most types of retinal ganglion cells, including parasol and midget cells, and also about half of the mcRGCs, proceed to the visual cortex via the lateral geniculate nucleus (LGN). The visual cortex is a massively interconnected set of visual processing areas. Many of these visual cortical areas are also multiply and reciprocally connected to the midbrain via the pulvinar areas [for further information see S. Shipp, "The functional logic of cortico-pulvinar connections", *Philos Trans R Soc Lond B Biol Sci*, 29 Oct. 2003, Volume 358 (1438), Pages 1605-1624; and S. Clarke, S. Riahi-Arya, E. Tardif, A. C. Eskenasy and A. Probst, "Thalamic projections of the fusiform gyms in man", *Eur J Neurosei*, May 1999, Volume 11 (5), Pages 1835-1838].

Higher centres within the extrastriate visual cortex then communicate with the PON providing about half its input nerve supply [again, see P. D. Gamlin, "The pretectum: connections and oculomotor-related roles", *Prog Brain Res*, 2006, Volume 151, Pages 379-405]. Among the various signals computed in the cortex is distance information derived from the binocular disparity between the eyes. This controls the so called triad of responses that occurs when objects loom near to us, whereby the eyes verge inward, the lens of the eye accommodates, and the pupils constrict. Presumably, the pupil constriction aids near vision by increasing the depth of field. Obviously the accommodative triad requires information about depth and that information is provided to the PON by its binocular cortical inputs. The accommodative response is known to contain input from the luminance and red-green input systems mentioned above that also proceed to the PON via the visual cortex [for further information see F. J. Rucker and P. B. Kruger, "Accommodation responses to stimuli in cone contrast space", *Vision. Res*, November 2004, Volume 44 (25), Pages 2931-2944]. The spectral colour sensitivity of the human luminance system is provided by the sum of red and green sensitive cone inputs, leaving the net peak spectral sensitivity corresponding to yellow hues.

Another input to the pupil that likely derives from the visual cortex are the pupillary responses to achromatic, equiluminant, high spatial frequency patterns, which permit visual acuity to be assessed via the pupillary responses, even in children [see J. Slooter and D. van Norren, "Visual acuity measured with pupil responses to checkerboard stimuli", *Invest Ophthalmol Vis Sci*, January 1980, Volume 19 (1), Pages 105-8; or K. D. Cocker and M. J. Moseley, "Development of pupillary responses to grating stimuli", *Ophthalmic Physiol. Opt*, January 1996, Volume 16 (1), Pages 64-67].

Therefore, the pupil has at least two possible sources of sensitivity to yellow luminance stimuli: the Yellow-ON response component of the mcRGCs and that of the parasol cells, the main constituents of the projection to the magnocellular layers of the LGN. The parasol RGCs have a rapid gain control mechanism that makes the parasol RGCs preferentially responsive to low spatial frequencies and high temporal frequencies [see E. A. Benardete, E. Kaplan and B. W. Knight, "Contrast gain control in the primate retina: P cells are not X-like, some M cells are", *Vis Neurosci*, May 1992, Volume 8 (5), Pages 483-486]. The yellow-ON component of the mcRGCs does not seem to have such a gain control mechanism.

Overall, the diverse nerve supply to the pupil means that the pupil can potentially report on the activity of a large proportion of the optic nerve fibres, and various parts of the visual thalamus and cortex. These various parts of the visual nervous system can all affect one common form of visual testing done on human subjects, which is characterising the extent and function of the visual fields of the eyes.

Human visual fields are commonly assessed by static perimetry. The basic form of this assessment involves sequentially presenting small visual test stimuli one after the other to each of a pre-set array of locations across the visual field. During the test, subjects indicate subjectively whether or not the subjects have seen each test stimulus that the subjects have been presented with, whilst the subjects maintain their gaze on a fixation target for the duration of the test. For most perimeters, subjects give behavioural responses, such as button presses, to indicate when the subjects have detected a test stimulus. Component parts of the visual field can have characteristic visual abilities. The goal of perimetry is thus to assess the visual ability or abilities of each part of the measured portion of the visual field. This generalises to other sensory systems, such as pressure on the skin or temperature of the skin where the skin is tiled in sensory fields for each sensation, or audio-visual space, around a person. One may wish to make a map of which parts of the sensory field have normal, supernormal, or abnormal sensory function. A difference from normal performance at any sub-region of the visual field is often referred to as a deviation and if a particular deviating part of the field performs significantly worse than normal in some aspect then that test region is said to have a field defect.

Unrelated technologies are used to assess properties of the pupils of the eye, for example, devices that measure the static size of the pupil under particular viewing conditions are referred to as pupillometers and devices that monitor the changing size of pupils over time are referred to as pupillographs. The distinctions between such devices are outlined by the USA Food and Drug Administration. Pupillographs have previously been used in conjunction with standard perimetry stimuli to measure responses to those stimuli and provide perimetric maps of the visual fields. However, these systems have proved to be unreliable and have not achieved commercial form or acceptance.

There are many reasons to assess the visual fields. For example, the visual fields are fundamentally limited by physical features of the face, such as the nose, brow ridges, and cheek bones, which change during development. Therefore, assessing the visual fields can be useful for tracking facial development or examining if a normal person's facial features provide the person with a suitable visual field, for example, for use in certain sports or occupations. The visual nervous system continues to develop until adulthood and this can affect aspects of the visual field. Therefore, visual field testing can be used to determine the state of a young person's development. Physiological stress testing can also reversibly alter the visual fields. Therefore, the availability of a rapid mechanism or technique to test the visual fields before, during, and after the stress test is beneficial for stress level assessment. Visual field testing can also be useful in the management of disease rather than assisting in diagnosis per se. For example, a doctor could use repeated visual field testing over a period of some years to determine if a course of treatment was either preventing further decline of visual function, or whether some stronger intervention was needed. Visual field testing can therefore be used to assist in the management of a variety of visually dependent issues.

Similarly other diseases, such as glaucoma, can cause localised damage to smaller areas of the visual field. Again these diseases are amenable to current, and presumably future, treatments so visual field testing is useful to determine the effectiveness of treatment over time. Of course, this means visual field testing can be useful in providing data that would assist a physician, in conjunction with other data, to make a diagnosis of a disease such as glaucoma or other disease that affects the visual function of the subject. In the case of glaucoma, other data that would assist to confirm glaucoma, once a visual field defect had been observed with field testing, would include: eye pressure tests, measurement of the thickness of the nerve fibre layer of the retina by means of polarimetry or optical coherence tomography (OCT), and or the topography of the head of the optic nerve, often called the optic disc, by visual inspection, stereo fundus photography, OCT or confocal microscopy. These would normally be performed in conjunction with other tests such as magnetic resonance imaging, positron emission spectroscopy of the brain or electroencephalography, to eliminate brain-related sources of the visual field defect such as stroke.

Perimetry is also used in other eye diseases that might cause localised damage to the retina resulting in defective function within a patch of the visual field such as age-related macular degeneration (AMD) or diabetic retinopathy (DR). One objective is to determine if the patchy visual field defects correspond to any features observed on or in the retina observed with a fundus camera, optical coherence tomograph, or similar device. In addition to assisting a health professional to make a diagnosis, the outputs from perimetry and other measures can be used to determine the risk that a given eye might develop AMD or DR in future.

The primary drawback with existing static perimeter systems, however, is the subjective nature of the testing, which causes the tests to suffer from inaccuracies and human/patient error since the current tests rely on the patient's ability to respond behaviourally to their detection of a stimulus (static perimeters do not use pupillary responses). Typically, the patient has a limited window of time in which to respond to the stimulus and can only be presented with a limited number of stimuli within a practical test period. Therefore, if the patient is not concentrating, some false positive or false negative responses are delivered and the perimetry device is not able to establish visual sensitivity well, thus compromising the accuracy of the test. The test may also be compromised by the patient's inability, or lack of desire as in cases of malingering, to respond to the stimulus accurately, which may be caused by any number of variables for example whether the patient suffers from autism, age-related disorders, and drug impairment or intoxication to name a few.

A further disadvantage of current tests is the time in which a test may be completed. Since the patient must respond subjectively to each stimulus, this places a limit on the time in which the test may be conducted.

An objective alternate method for mapping the visual fields is to employ so-called multifocal methods. In these methods, one uses an array of visual stimuli, each member of the array being presented to a particular sub-region of the visual field. The appearance or non-appearance of stimuli at each sub-region of the visual field is modulated by temporal sequences that are mutually statistically independent. Optimally, the modulation sequences should be completely statistically independent, that is the modulation sequences should be mutually orthogonal, which is to say having zero mutual correlation. A variety of patents related to various orthogonal sequences [see U.S. Pat. No. 5,539,482 (U.S. Ser. No. 08/025,423) issued 23 Jul. 1996 to T. L. Maddess & A. C. James, the disclosure of which is wholly incorporated herein by reference] and near orthogonal sequences [see for example U.S. Pat. No. 4,846,567 (U.S. Ser. No. 06/893,789) issued 11 Jul. 1989 to Sutter] exist, but recent analysis methods permit more general stimuli to be used [see, for example: U.S. Pat. No. 6,315,414 (U.S. Ser. No. 09/647,357) issued 13 Nov. 2011 to T. L. Maddess & A. C. James; U.S. Pat. No. 7,006,863 (U.S. Ser. No. 10/239,971) issued 28 Feb. 2006 to T. L. Maddess & A. C. James; and International (PCT) Patent Publication No. WO/2005/051193 (PCT/AU2004/001656) published on 9 Jun. 2005 in the names of The Australian National University, T. L. Maddess & A. C. James; the disclosures of the three documents are wholly incorporated herein by reference).

The basic idea of multifocal methods is that the temporal statistical independence of the stimuli permits trains of many stimuli to be presented concurrently to different parts of a sensory field, for example at different regions of the visual field, or different stimulus conditions, each driven by its own sequence. Then the estimated responses to presentations at all the test locations, which may be one or more so-called weighting functions, may be recovered from recordings of pooled neural activity of the visual nervous system. The weighting functions can characterise linear responses and non-linear responses and interactions. The neural responses to the stimuli can be recorded by electrical or magnetic detectors, changes to the absorption, scattering or polarization of infrared light or other electromagnetic radiation from parts of the nervous system, or functional magnetic resonance imaging. As can be appreciated, sensors for detection of such neural responses are complex and rely on correct placement for efficient operation, typically on or near the scalp or eye of the patient. Also, methods such as electroencephalography suffer from the fact that different subjects have different brain anatomy and this affects the signals measured on the scalp. Subjects are also often averse to the placement of electrodes on their scalp or eyes, and there are health risks associated with any such contact method. Responses to the stimuli may be detected through monitoring of the pupils, which have the advantage of permitting non-contact assessment, but to date there are no commercial perimetry systems that use pupillography to do multifocal testing of the nervous system.

The following description summarises features of multifocal methods that make multifocal methods distinctive. U.S. Pat. No. 5,539,482 discloses the use of independent multifocal stimuli to be presented to the two eyes in order to determine responses generated in the brain just after the point where the inputs from the two eyes first come together, that is just after the first optic chiasm, using so called binocular interaction kernels. No other spatial or temporal constraints on those multifocal stimuli are made. U.S. Pat. No. 7,006,863 discloses that a particular temporal constraint is optimal. In particular, U.S. Pat. No. 7,006,863 discloses that presentations of transient valid stimuli at any location in the multifocal stimulus array should be interleaved with longer aperiodic sections of non-valid, null, stimuli, such that the mean rate of presentations of the valid stimuli at any one region of the stimulus ensembles is between 0.25 and 6 presentations per second. This means on any time step in the temporal stimulus sequence the probability of a valid stimulus appearing at a given single locations is, $p_{single}$, which is $\ll \frac{1}{2}$. Since no constraint is made on when any two spatially adjacent neighbouring regions should appear relative to each other, two spatially adjacent neighbouring regions co-appear at probability=$p_{pair}$, which is exactly equal to $p_{single} \times p_{single} = p^2_{single}$. These multifocal stimuli are said to be temporally sparse. International (PCT) Patent Publication No. WO/2005/051193 applies a further constraint that when a stimulus appears at a given location that the probability of a spatially adjacent stimulus appearing, $p_{pair}$, is $\ll p^2_{single}$, and preferably $p_{pair}=0$ for adjoining stimulus regions. These stimuli are said to be spatially-sparse, since immediately adjacent neighbouring stimuli either tend not to co-appear, or never co-appear. In all of the above three methods, the stimuli can be seen to be presented rather evenly across the visual field, particularly in the case of the spatially-sparse stimuli, and almost never, or never, occur in volleys of spatially adjacent clusters of stimuli.

Overall, a need exists for a rapid objective, non-contact visual field assessment, which can also be used for other purposes such as determining the focus of localised visual attention, and or interactions between other sensory fields and the visual field, for example the auditory field, or the somatosensory field.

SUMMARY

The pupils are an excellent substrate for recording neural responses of the visual nervous system. The pupillary system has special properties described hereinafter that can be harnessed to provide more reliable responses from parts of the visual or other sensory fields for which a response can be obtained from the pupillary system.

Further, the method is designed to enhance the responses of the pupils to aid in other assessments of the visual system that can employ one or both pupils in human or animal subjects. This method and apparatuses or systems for implementation of the method as described hereinafter are of use when the pupils are used to assess any collection of these functions or collections of visual stimuli, allowing the pupillary responses to desired subsets of functions and stimuli to be enhanced relative to the others in the total set being tested.

According to an aspect of the invention, there is provided a method for assessing the nervous system of a subject. The method comprises the step of presenting a sequence of selected individual stimuli from a set of at least two stimulus ensembles to the nervous system of a subject. The stimulus ensembles each comprise a plurality of individual stimuli and the plurality of individual stimuli within an ensemble constitute a spatially adjacent cluster within a subregion of the sensory field. The presentation of each of the individual stimuli within any clustered ensemble is governed by pseudorandom sequences that are statistically independent. Accordingly, the control by the pseudorandom sequences means that on a given time-step of the presentation only a subset of the individual stimuli within an ensemble are presented. Thus, the presented ensembles cannot collectively make a consistently represented pattern such as a checkerboard or other periodic pattern across the sensory field, because on any given presentation of an ensemble a different subset of the stimuli defining the ensemble is presented. The individual stimuli of any ensemble may themselves display a periodic pattern across their region of the sensory field. The control by the pseudorandom sequences means that on a given presentation of a given ensemble some individual stimuli may be concurrently presented. The sequence of selected individual stimuli is adapted to evoke pupillary responses in at least one pupil of the subject. The method may further comprise the step of detecting, using a sensor, responses of at least one pupil evoked by the stimuli. The method may further comprise the step of relating the detected pupillary responses to the function of the subject's neural responses to at least two of the individual stimuli of each of the ensembles.

The individual stimuli may be visual stimuli. The visual stimuli may be presented to a subject at multiple regions in the subject's visual field concurrently where the regions are confined to ensembles of spatially adjacent clusters of stimuli. The ensembles of clustered stimuli may form roughly arcuate portions of the visual field that surround the centre of the visual field of a subject's eye. These arcuate regions may extend from the centre of the visual field in polar coordinates from a first inner radius to a second outer radius, and from a first polar angle to a second polar angle. The arcuate portion of the field defining a clustered ensemble of individual stimulus regions may have borders that define one or more quadrants of the visual field. The borders of the arcuate portions may be defined by the horizontal and vertical meridians of the visual field. Alternatively, the ensembles of clusters of individual stimuli may be defined on rectilinear coordinates within the visual field but may similarly be constrained to portions of the visual field within quadrants or multiples of quadrants of the visual field. The borders of these portions of the visual field defined on rectilinear coordinates may include the horizontal and vertical meridians of the visual field. The ensembles of individual visual stimuli may be presented to a subject within multiple clustered ensembles within in the visual field of one or both of the subject's eyes. The presentation of the set of ensembles may alternate in a round robin or pseudorandom fashion. The resulting set of pupillary responses evoked by each of the visual stimuli provides a map of visual function across the tested portion of the visual field of the one or both eyes. The visual stimuli may thus be monocular or binocular and presented separately or concurrently. The mean inter-stimulus interval period may be selected to be between 1 seconds/region and 16 seconds/region and preferably about 4 seconds/region. Alternatively the broader range of 0.1 seconds/region to 100 seconds/region may be selected.

The visual stimuli at one or several locations may alternate between one of a number of stimulus conditions. The stimulus conditions may be selected from the group consisting of stimulus luminance level, stimulus colour or hue. The stimulus conditions for each stimulus in the ensemble may each be controlled by a unique statistically independent sequence such that the pupillary responses are representative of the neural responses affected by a stimulus space spanned by those stimulus conditions.

Binocular visual stimuli may be adapted to emulate objects that change in depth at different regions of the visual field. The measure of the distance to objects in the visual field may be determined by presenting stereo disparity cues to each of the subject's eyes, such that the pupillary responses are representative of the function of the accommodative system of the subject's eyes.

The method may further comprise the step of recording the pupillary responses of a selected one of the two retinas. The method may further comprise the step of characterising the pupillary response of the retina associated with the recorded pupil by the direct pupil response. The method may further comprise the step of and characterising the pupillary response of the other retina by the consensual response of the recorded pupil.

In an exemplary arrangement, the method may further comprise the steps of: concurrently presenting ensembles of unique visual stimuli to the other eye of the subject; recording the pupillary responses of a selected one of the two retinas; characterising the pupillary response of the retina associated with the recorded pupil by the direct pupil response; and characterising the pupillary response of the other retina by the consensual response of the recorded pupil.

An array of stimuli may be an array of auditory stimuli present at different azimuth and elevation angles around the head, or an array of audio visual stimuli that where audio and visual stimuli are present together or separately at different azimuth and elevation angles around the head. The array of stimuli may test shifts in the attention of a subject at different parts of a sensory field. The array of possible stimulus regions may be subdivided into clustered ensembles of stimuli to be selected for possible co-presentation on a given time step. The method may further comprise the step of recording the pupillary response of the subjects' evoked by the array of stimuli. In an exemplary arrangement, the method may further comprise the steps of recording the pupillary response of the subjected evoked by the array of stimuli; and characterising the function of those neurally mediated attentional, emotional or mental health mechanisms of the subject from the recorded responses.

According to another aspect of the invention, there is provided a system for assessing the nervous system of a subject. The system comprises a source for generating sequences of stimuli. The source may be a computer or computer controlled system. The sequences of stimuli may be selected or derived from at least two stimulus ensembles. The sequences may be adapted to evoke pupillary responses in at least one pupil of the subject. The stimulus ensembles comprise a plurality of individual stimuli that are not fixed periodic or aperiodic ensembles of individual stimuli. The stimulus ensembles each cover substantial portions of the visual field and those portions of the field typically are defined within quadrants or multiples of quadrants of the visual field, typically defined by the horizontal and vertical meridians of the visual field. The system may further comprise a processor for recording and relating the detected pupillary responses to the function of the subject's neural responses to at least two of the individual stimuli of the ensembles.

The system may further comprise a database of recorded data stored in a physical recording medium, such as a computer readable recording medium. The recorded data comprises information on at least one or more of:

the strength or mean strength of the neural responses evoked in at least one subject by the individual stimuli;

the strength or mean strength of the pupillary responses evoked in at least one subject by the individual stimuli.

The stimulus generation source determines the at least one weighting function for each of the individual stimuli from an analysis of the recorded data.

BRIEF DESCRIPTION OF THE DRAWINGS

Arrangements of the methods, apparatus and systems are described, by way of an example only, with reference to the accompanying drawings, in which:

FIG. 1A is a simplified plan view of the afferent pathways from the two eyes via the chiasm to the two pretectal olivary nuclei (PONs), and then the efferent portion via a second chiasm to the two Edinger-Westphal nuclei (EWN) and then onto the chary ganglia;

FIG. 1B is a simplified view of the pathways shown in FIG. 1A, which are used in FIG. 12;

FIG. 4 illustrates a particular non-limiting example of ensembles of stimulus regions like those in FIG. 3 that define arcuate portions of the visual field that each are limited to the left or right hemifield of the eye of a test subject are defined, and these ensembles are presented in a round robin fashion to the two hemifields of the two eyes of a test subject in a so called clustered-volley design, where on each time step any particular region of the presented ensemble being controlled by its own statistically independent pseudorandom sequence has a probability of one half of actually being presented and described in FIG. 5 and depicted in FIG. 6;

DETAILED DESCRIPTION

Figure 2:
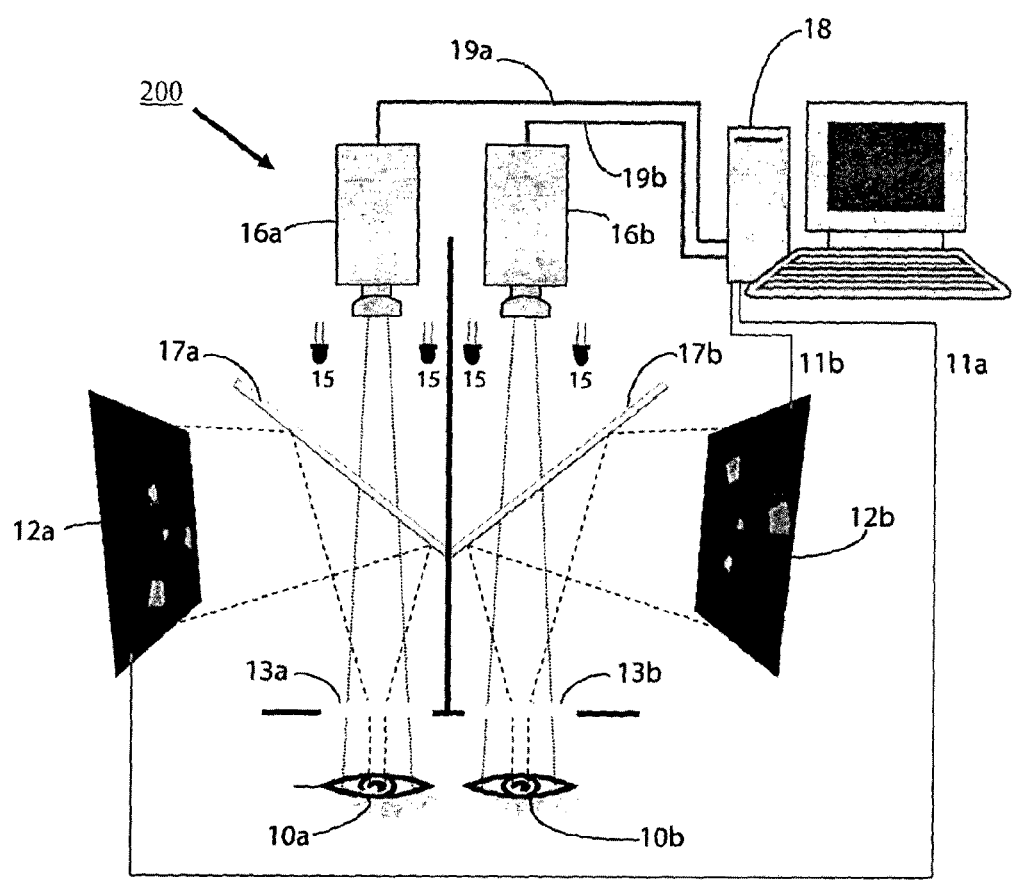
FIG. 2 is a block diagram illustrating components of a non-limiting design of a device for presenting independent sequences of visual stimuli to the two eyes of a test subject via two display devices and mirrors that are transparent in the infrared and recording the changes in diameter of the two pupils using two video recording devices, and a processor for controlling the presentation of the sequences of test stimuli and for analysis of the pupil diameter data.

The embodiments of the invention have been developed primarily for use as methods and apparatuses for improved assessment and quantification of the visual fields field of human and animal subjects, in both health and disease, and are described hereinafter with reference to this application. It will be appreciated, however, that the invention is not limited to this particular field of use. In particular, the methods and apparatuses described herein may also be applicable for assessment of visual accommodation, visual acuity, hearing and audio-visual function, emotional state, drug use, and attentional disorders.

Unless defined otherwise, all technical and scientific terms used herein have the same meaning as commonly understood by those of ordinary skill in the art to which the invention belongs. For the purposes of the present invention, the following terms are defined below.

The articles "a" and "an" are used herein to refer to one or to more than one (i.e. to at least one) of the grammatical object of the article. By way of example, "an element" refers to one element or more than one element.

The term "about" is used herein to refer to frequencies or probabilities that vary by as much as 30%, preferably by as much as 20%, and more preferably by as much as 10% to a reference frequency or probability.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

With reference to FIG. 1A, the pupil system as the system has evolved seems to involve a gain control system that tends not to attenuate responses to light stimuli that are clustered together in any large part of the visual field. This is an important point in respect of the embodiments of the invention. In the embodiments of the invention, the stimuli are presented in volleys of spatially adjacent clusters of stimuli. Advantageously, the embodiments of the invention concern an unrelated spatial constraint operated on sub-sets of multifocal stimulus ensembles to ameliorate the effects of a particular gain control found to be operating at or after the level of the EWN. This gain control system tends to diminish responses of the pupil less when multiple visual stimuli are presented in volleys of spatially adjacent clusters of stimuli, compared to earlier methods such as temporally or spatially sparse stimuli.

The embodiments of the present invention seek to substantially overcome or at least ameliorate one or more of the disadvantages of existing systems and methods, or at least to provide a useful alternative, particularly when it is desirable to concurrently present test stimuli across an array of sub-regions of a sensory field (e.g., visual, auditory or other stimuli detectable via a pupillary response), where the sensory function is overseen by gain control mechanisms that suppress responses of the pupils to stimuli that are presented diffusely across the visual field, but suppresses responses less if the same number of stimuli are delivered in volleys of spatially adjacent stimuli that collectively span a substantial subset of the visual field, such as a hemifield, extending out to 10 to 50 degrees radius from the centre of the visual field.

FIG. 1A shows relevant parts of the pupillary response pathways showing how visual inputs to the left and right halves of each retina 1 flow up the two optic nerves 2 and onward to the pupils. Information from the two half retinas that are on the nasal side of each eye cross at the optic chiasm 3 such that information from the two left half retinas converge at the left pretectal olivary nucleus (PON) 4, and the two right hemi-retinas converge at the right PON. There is then a second decussation (crossing over) 5 such that each Edinger-Westphal nucleus (EWN) 6 receives inputs from all four hemi-retinas. The PONs 4 also receive input from the visual cortex but that is not shown, but those cortical areas are supplied by input from the two eyes much for the subcortical pathways depicted in FIG. 1A. In this way, each pupil can respond to both hemifields of both eyes. This defines two types of pupil responses: a direct response when a pupil responds to stimulation of its own eye, and a consensual response when a pupil responds to stimulation of its fellow eye. For this reason, only one pupil may be monitored to obtain information about activity in the two retinas. Advantageously, monitoring both pupils at the same time as this permits a user to distinguish localised changes in the visual field that correspond to changes in the afferent pathway: from eye to brain, and on the efferent pathway, from the brain to the pupil. FIG. 1B shows a simplified version of the pathways that is used hereinafter.

An example of a suitable apparatus 200 for presenting the multifocal stimulus and recording the pupillary responses as per the methods disclosed herein is illustrated in FIG. 2. The stimulus configuration in the present arrangement is a dichoptic one, which provides independent stimuli to the two eyes (that is, each eye sees a different, independently controlled stimulus pattern and or sequence during a test). The independent stimuli for the test subject's left and right eyes 10a and 10b respectively were created by the computer 18 and conveyed on respective communication lines 11a and 11b to be displayed on two liquid crystal displays (LCDs) 12a and 12b. Positive lenses 13a and 13b of equal focussing power (focal length) disposed before the test subject's eyes 10a and 10b are used with the focal length selected such that the displays 12a and 12b appear to be at far focus, i.e. visual infinity. This also allows normal corrective lenses, as in eye glasses or contact lenses, to be used (not shown) to correct for any refractive errors of the eyes 10a and 10b. Infrared light to illuminate the eyes is provided by light emitting diodes (LEDs) 15, and the contractions of the irises, which change the pupil diameter, are recorded by detectors 16a and 16b for recording the responses of each iris separately. The detectors 16a and 16b may be video cameras, CCD detectors, photodiode detectors, simple power detectors or other suitable detectors for recording the reflected infrared light reflected from the subjects' eyes 10a and 10b. Two dichroic mirrors 17a and 17b are used to reflect the image of a respective LCD screen to one of the subject's eyes whilst allowing infrared light from the LEDs 15 to pass through to illuminate the subject's eyes 10a and 10b and also to allow reflected infrared light to be transmitted back through the mirrors 17a and 17b to be detected by detectors 16a and 16b, and communicated to computer system 18 for analysis by respective communication lines 19a and 19b.

Figure 3:
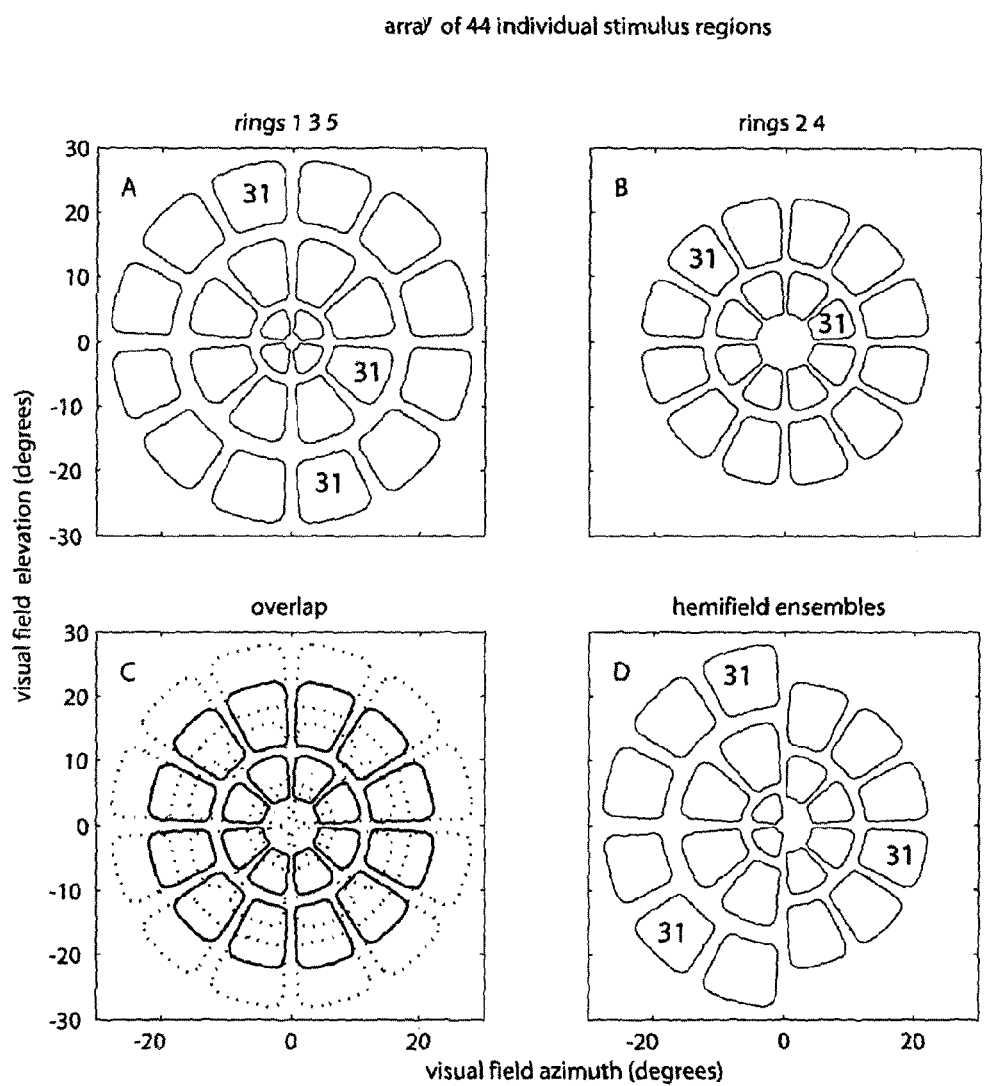
FIG. 3 shows graphs depicting 44 regions of an array of multifocal stimuli array presented within the central 60 degrees of the visual field consisting of sets of rings of stimulus regions, central ring 1 to outer ring 5, that if presented simultaneously would overlap, but when parsed into ensembles of clusters of regions drawn from of rings 1, 3, 5 or rings 2 and 4 that only stimulate portions of the left or right hemifield, the visual field do not overlap in space during the stimulus presentation sequence, the contours thus represent the boundaries of stimulus regions within which a visual stimulus may be presented at a given time step of the stimulus sequence as illustrated in FIG. 6.

FIGS. 3A, 3B, 3C and 3D together show the boundaries of an array of 44 regions of the visual field, each of which regions could each display a visual stimulus. These bounded regions displaying a stimulus are referred to as stimulus regions 31, only some of the 44 possible stimulus regions of the array being labelled with 31 to prevent clutter in FIG. 3. The centre of each plot represents the centre of the visual field, also known as the point of fixation, and the horizontal and vertical axis labels (visual field azimuth (degrees) and visual field elevation (degrees)) indicate that this particular array covers most of the visual field within the central 60 degrees of the visual field about the point of fixation. To test the visual field, the test subject must fixate the centre of the test array for the duration of the test. The detectors 16a and 16b may therefore also be used to monitor the positions of the eyes 10a and 10b and the adherence of the subject to fixation of the centre of the array over the course of the test. In this particular non-limiting design, the array of stimulus regions consists of 5 rings of regions. As shown in FIG. 3A, the centre ring consisting of 4 stimulus regions is referred to as ring 1 and the outer ring of 12 stimulus regions is referred to as ring 5. The centres of rings 2 and 4, FIG. 3B, are at intermediate radii to rings 1, 3, 5, and so as shown in FIG. 3C overlap with each other if selected stimuli from rings 1,3,5 are presented at the same time as stimuli from rings 2 and 4. According to the embodiments of the present invention, the array of stimulus regions is divided into clustered ensembles preferably on the basis of quadrants of the visual field, or sums of quadrants. One such arrangement that is used hereinafter is illustrated in FIG. 3D where the array of stimuli has been partitioned into 4 clustered ensembles comprising the stimulus regions presentable to left and right halves of the visual field for either rings 1, 3, and 5 or rings 2 and 4; two of those clustered ensembles are illustrated in FIG. 3D.

The overlapping of the stimuli may be such that spatial aliasing of the stimuli on the sampling grid is minimised. That is, the stimuli may transmit little to no spatial frequencies that the sampling grid cannot represent accurately. The stimuli may alternatively or concurrently be configured such that, if presented simultaneously, individual stimuli may be sufficiently overlapping such that the individual stimuli transmit little to no spatial frequencies above the critical sampling frequency of the sampling grid, referred to as the Nyquist rate and defined by the geometry of the sampling grid. The profiles of the stimuli may be smoothly varying and/or blurred. The smoothly varying profiles of the individual stimuli (particularly at the edges and/or corners of the individual stimuli) may be sufficiently smooth such that the individual stimuli comprise only low-spatial-frequency Fourier components. In that case, the stimulus region boundaries shown in FIGS. 3, 4, 6, 7 and 8 represent a contour indicating the brightness at about the half maximal value, in which case the edges of the stimuli along their dim borders overlap in space. The profiles of the stimuli may be smoothly varying such that the individual stimuli contain only spatial frequencies that are less than or equal to the highest spatial frequency that can be represented by the sampling grid defined by the points of the sampling grid. The sufficiently smooth or blurred individual stimuli have the significant advantage that the subject may not be well refracted (that is, may have incorrect, insufficient or even no refractive correction) without significantly affecting the results of the assessment of the subject's visual field. These properties of the stimulus sampling grid and the individual stimuli are the subject of International (PCT) Patent Publication No. WO/2009/059380 (PCT/AU2008/001663) published 14 May 2009 in the name of The Australian National University, T. L. Maddess and A. C. James, the contents of which are incorporated herein by reference.

In the present arrangement, the array of stimulus regions is presented in a multifocal stimulus arrangement where the appearance or non-appearance of stimuli in individual regions is controlled by statistically independent pseudorandom sequences. Importantly, on any time-step of the sequence in which stimuli might be presented, only those stimuli regions from one clustered ensemble are eligible to display a stimulus. The clustered ensembles that may present a stimulus are exchanged in a round robin sequence that repeats over many cycles. FIG. 4 shows an arrangement where the 4 types of clustered ensembles defined in FIG. 3 are interleaved for presentation to the two eyes. In the figure, time proceeds diagonally from top left to bottom right and the pairs of figures at each time step indicate the stimulus arrangement presented to the left and right eyes by an apparatus like that of FIG. 2. A blank figure in FIG. 4, showing no stimulus region borders, indicates that no stimulus is presented to that eye on that time step. As indicated in FIG. 4, once the ensembles of clustered stimuli have been selected, the stimulus sequence repeats cyclically to produce a longer test sequence.

Importantly, the division into clustered ensembles means that the case that all of the stimulus regions are candidates for being displayed on any time step never occurs. Also, at times between the presentations, the displays showed an inactive state which was a background light level, and so was neither black, i.e. no stimulus, nor a wide field bright flash, nor was any other periodic stimulus interleaved between the times when stimuli were displayed. The time step used in the demonstrations used here is typically 0.25 seconds and therefore the stimuli that appeared with probability 0.5 when stimuli were candidates for being active, had a mean presentation interval of 4 seconds and so are temporally sparse as described in U.S. Pat. No. 7,006,863.

Notice that, due to the control by the pseudorandom sequences, the intervals when the background was presented are of random length.

Figure 5:
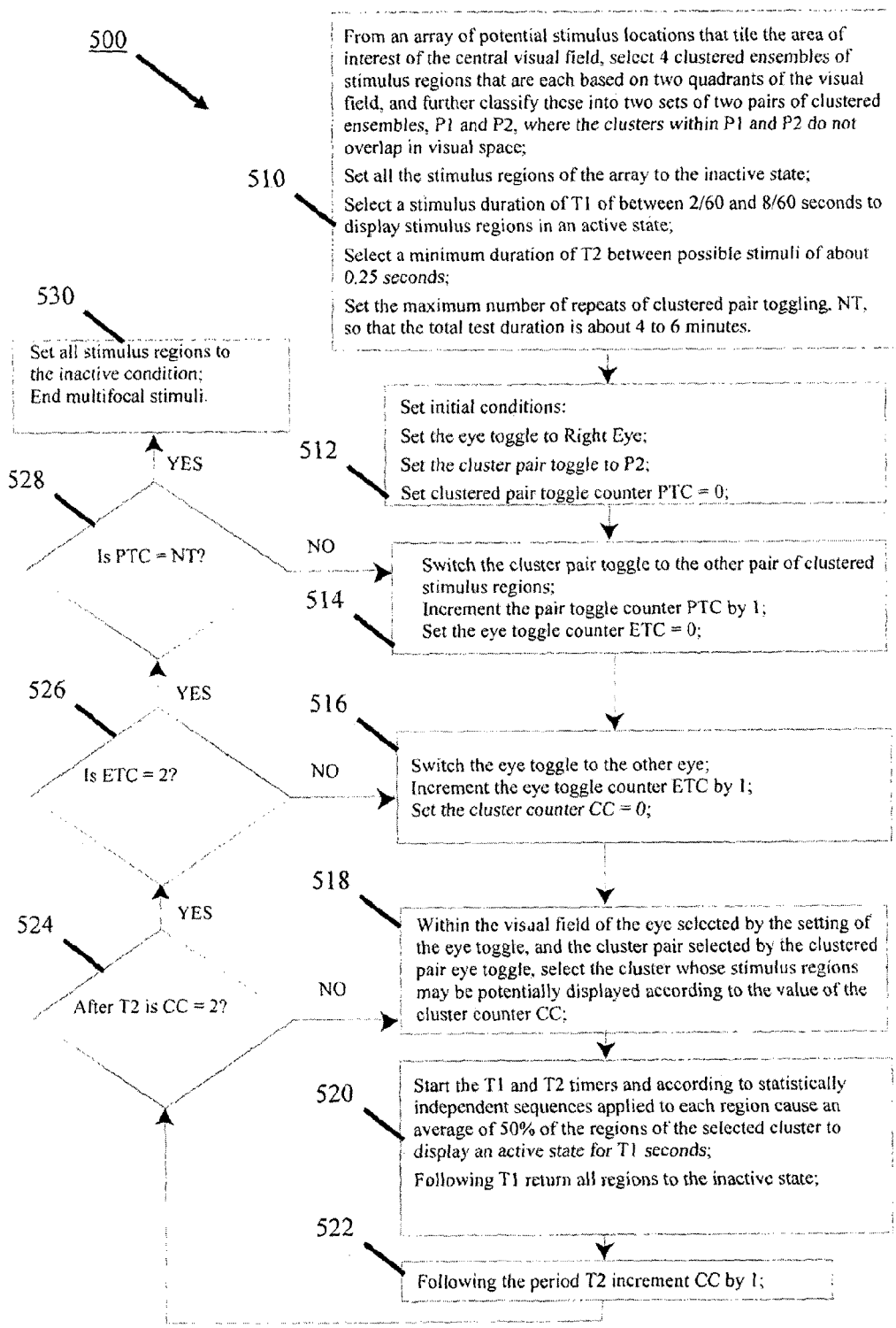
FIG. 5 is a flow chart of a method of producing the temporal evolution of a clustered volley multifocal stimulus sequence, including the steps in the non-limiting design of clustered-volley stimuli like those of FIG. 4 where first the array of stimulus regions that may potentially be presented are defined, clustered ensembles of subsets of those regions are defined, and then the stimulus process begins a number of presentation cycles in which the sets of clustered stimulus ensembles are selected and regions within each cluster are selected for presentation by statistically independent pseudorandom sequences.
Figure 6:
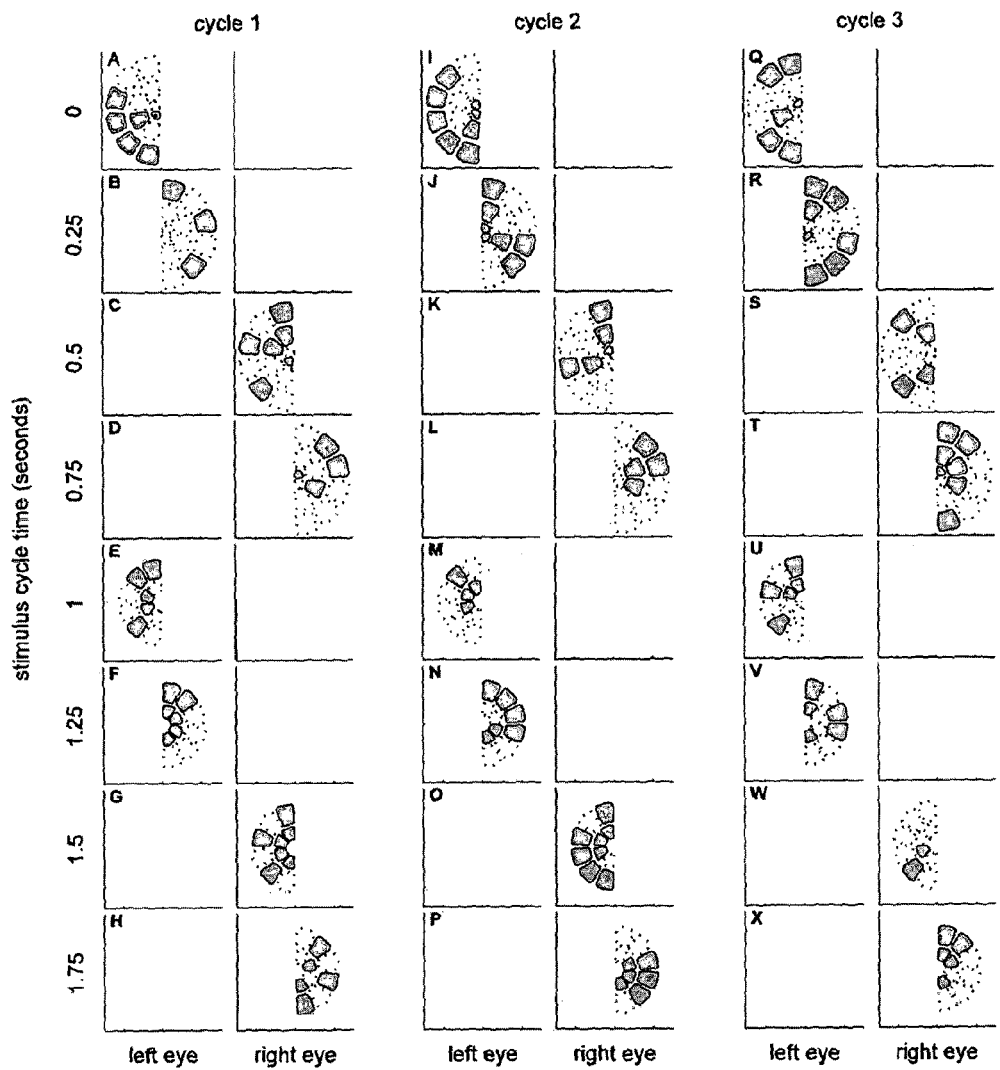
FIG. 6 illustrates the results of 3 cycles of a clustered-volley stimulus presentation process where the dotted contours indicate the regions of each ensemble where a stimulus may be presented, and the darkly coloured regions indicate the stimulus regions that on a particular cycle have actually presented a stimulus in an active state, where the dark colouring of the regions typically represents a bright region presented on a dimmer background field, but the active state of any single region might present flicker or a pattern within the boundaries of the region.

FIG. 5 shows a method 500 of producing the temporal evolution of a clustered volley multifocal stimulus sequence, including the steps of the non-limiting design presented in FIG. 4. Before the start of the test, the particular sets of clustered ensembles are selected. FIGS. 4, 6, 7 and 8 illustrate some possible non-limiting designs for the clustered ensembles of regions. As shown in FIGS. 4, 6, 7 and 8, four clustered ensembles are chosen and durations T1 and T2 defining the duration of each phase of the test multifocal stimulus sequences are set, and all the possible test regions within the visual field are set to an inactive state. Following the onset of the test, the round robin cycling of presentations of active stimuli within the clustered ensembles is run through until the total number of cycles is completed. Although FIGS. 4, 5 and 6 depict a design in which the stimuli cycle through the ensembles in a round robin fashion, clearly the ensembles could also be presented in a randomised order where particular ensembles are repeated on average at intervals of 2 to 8 seconds.

In non-limiting variations of FIG. 5 the long stimulus sequence of 4 to 6 minutes can be broken into segments of 30 to 40 seconds duration. Following each segment the person being tested can have a short rest of several to many seconds. The test can then continue when the person is ready to proceed. Notice that this would require a fourth loop between the ETC counter loop and the PTC loop of FIG. 5. Starting a stimulus sequence may cause a short-lived start-up transient in the pupillary response. Therefore, each segment of stimuli can usefully be preceded with about the last 1 second of the segment preceding the current stimuli segment and to later clip out that extra second from the beginning of the record of pupillary responses from each segment record before concatenating the segment records into a full stimulus record. The procedure of allowing test subjects a periodic break also allows segments to be repeated if the segments contained too many blinks or fixations losses. The methods described in this paragraph have been used in all the multifocal pupillographic experiments described herein.

A more detailed description of the method 500 follows. Each of steps 510, 512, 514, 516, 518, 520 and 522 has a number of sub-steps, as depicted in FIG. 5. However, it will be apparent to those skilled in the art that sub-steps could be separate steps, and the steps of FIG. 5 are merely organised to simplify the overall drawing. Processing comments at step 510. In step 510, from an array of potential stimulus locations that tile the area of interest of the central visual field, 4 clustered ensembles of stimulus regions are selected that are each based on two quadrants of the visual field. These selected ensembles are further classified into two sets of two pairs of clustered ensembles, P1 and P2, where the clusters within P1 and P2 do not overlap in visual space, as in 141 and 142 or the clusters of FIG. 4, FIG. 5, or FIG. 6. In step 510, all the stimulus regions of the array are set to the inactive state. A stimulus duration of T1 of between $2/60$ and $8/60$ seconds duration is selected to display stimulus regions in an active state. A minimum duration of T2 between possible stimuli of about 0.25 seconds is selected. The maximum number of repeats of clustered pair toggling, NT, is set so that the total test duration is about 4 to 6 minutes.

In step 512, initial conditions are set, the eye toggle is set to Right Eye, the cluster pair toggle is set to P2, and clustered pair toggle counter PTC is set to zero (PTC=0).

In step 514, the cluster pair toggle is switched to the other pair of clustered stimulus regions, the pair toggle counter PTC is incremented by 1, and the eye toggle counter ETC is set to zero (ETC=0).

In step 516, the eye toggle is switched to the other eye, the eye toggle counter ETC is incremented by 1, and the cluster counter CC is set to zero (CC=0).

In step 518, within the visual field of the eye selected by the setting of the eye toggle, and the cluster pair selected by the clustered pair eye toggle, the cluster whose stimulus regions may be potentially displayed is selected according to the value of the cluster counter CC.

In step 520, the T1 and T2 timers are started, and according to statistically independent sequences applied to each region an average of 50% of the regions of the selected cluster are caused to display an active state for T1 seconds. Following T1, all regions are returned to the inactive state.

In step 522, following the period T2, cluster counter CC is incremented by 1. Processing then continues at decision step 524.

In decision step 524, a check is made to determine after period T2 if the cluster counter CC is equal to 2. If decision step 524 returns true (Yes), processing continues at decision step 526. Otherwise, if decision step 524 returns false (No), processing continues at step 518.

In decision step 526, a check is made to determine if the eye toggle counter ETC is equal to 2. If decision step 526 returns true (Yes), processing continues at decision step 528. Otherwise, if decision step 526 returns false (No), processing continues at step 516.

In decision step 528, a check is made to determine if the clustered pair toggle counter PTC is equal to the maximum number of repeats of clustered pair toggling NT. If decision step 528 returns true (Yes), processing continues at step 530. Otherwise, if decision step 528 returns false (No), processing continues at step 514.

In step 530, all stimulus regions are set to the inactive condition, and the multifocal stimuli end. Thus, method 500 terminates.

FIG. 6 shows an example of 3 possible cycles of the stimulus sequences illustrated in FIGS. 4 and 5. As in FIG. 4, there are 4 possible selections of clustered ensembles of stimulus regions whose individual stimulus regions are candidates for presentation on each time step. Also as in FIG. 4, the same set of 4 clustered ensembles, are shown as being presented interleaved to the two eyes to make 8 cluster and eye conditions that are repeated in a round robin fashion. Due to the controlling influence on the pseudorandom sequences, each of the regions within the each ensemble has probability one half of displaying an actual stimulus within its boundaries, and those regions that are selected to display a valid stimulus are said to be active. In FIG. 6, the active regions on any given time step are shown filled in with grey. In FIG. 3, the numerals 31 are used as a marker to indicate which elements are referred to as stimulus regions, but one could image the numerals 31 to be markers of regions that are active in a multifocal sequence, like the dark filling of some regions in FIG. 6, those regions adopting an active state in a probabilistic fashion. Given that the stimuli that are active appear in volleys within clusters, this is referred to as the clustered-volley method or design. The background of each stimulus field was yellow at 10 cd/m² and when active the stimulus regions were much brighter yellow with a maximum of 150 cd/m². In practice, the maximum value of the active stimulus regions varied somewhat across the visual field, so that regions that were more sensitive received somewhat dimmer stimuli to make the responses of a normal subject more similar across the field. This follows the stimulus balancing method disclosed in International (PCT) Patent Publication No. WO/2010/063064 (PCT/AU2009/001560) published on 10 Jun. 2012 in the names of The Australian National University, T. L. Maddess, and A. C. James, the contents of which are incorporated herein by reference. It is evident from FIG. 6, the active stimulus regions on any time step do not by design create amongst themself a periodic pattern; instead, on any given time steps, the displayed regions tend to form a random pattern across the regions of their ensemble. Note that one possible stimulus variant would allow a given stimulus region to display a small periodic pattern within its boundaries rather than a solid colouring as illustrated in FIG. 6.

Figure 7:
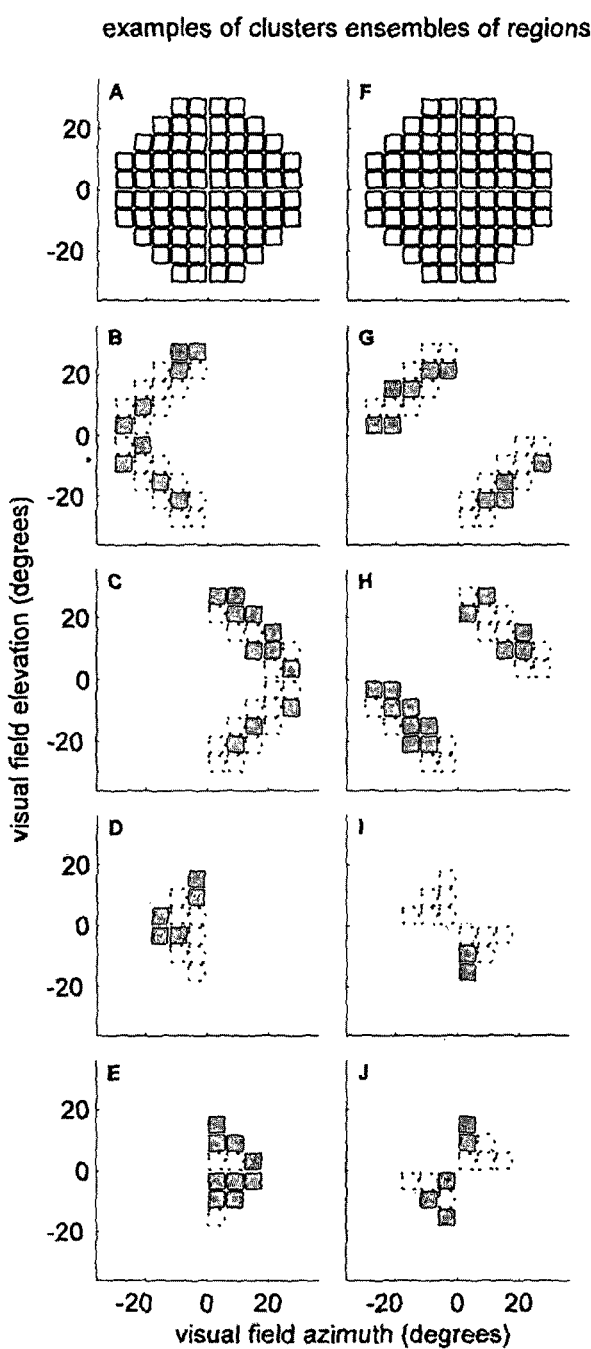
FIG. 7 illustrates two alternative non-limiting designs of an array of visual stimuli, illustrated by the small boxes in the FIGS. 7A and 7F, and their partitioning into one example of quadrant based ensembles of clustered stimulus regions within the visual field as illustrated by FIGS. 7B to 7E, and a different quadrant based ensemble of clustered locations within the visual field as illustrated by FIGS. 7G to 7J, where, as in FIG. 6, the action of the pseudorandom sequences upon which regions might show an active stimulus on a given time-step is illustrated by the dark coloring of some of the regions of each clustered ensemble.
Figure 8:
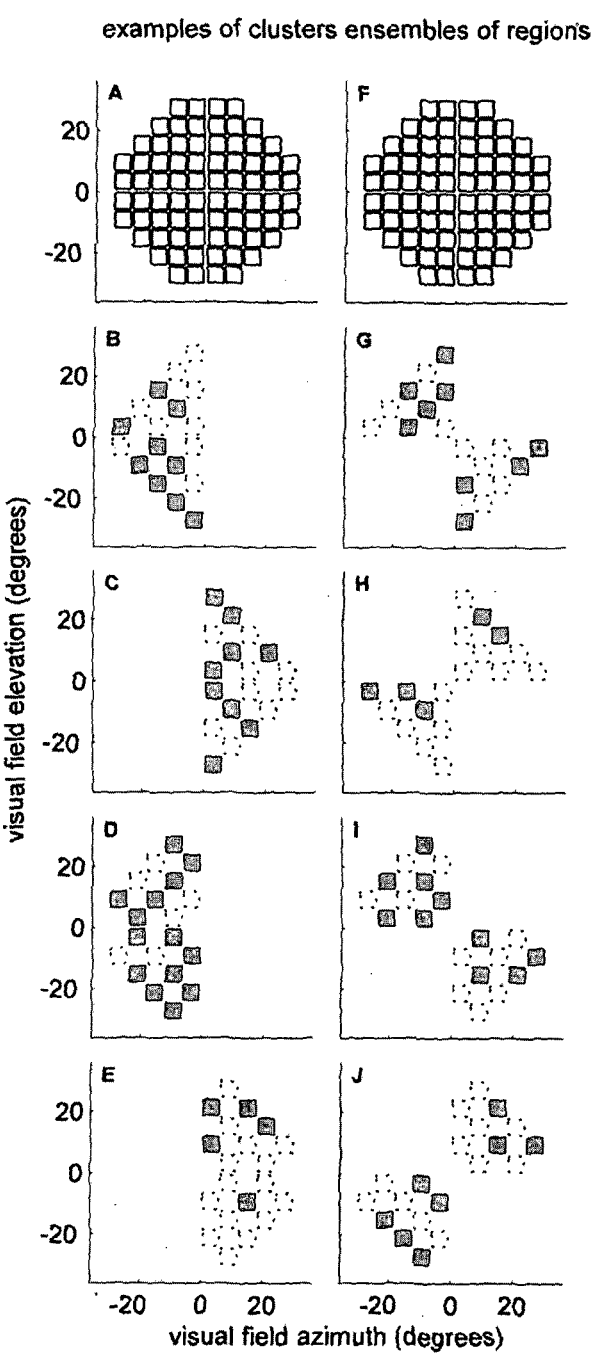
FIG. 8 shows a figure similar to FIG. 7 but where the stimulus regions are assigned to two different sets of quadrant based clustered ensembles where the assignment into a given cluster is based on the alternate diagonal lines of regions within the total array defined by FIGS. 8A and 8F.

FIGS. 7 and 8 show four non-limiting alternative versions of the clustered-volley design. Here the rectilinear array of square-shaped regions of the visual field where stimuli could be potentially be presented are shown in FIGS. 7A and 7F and FIGS. 8A and 8F, and the figures showing the array are shown twice for easy comparison with the figures below. As in FIG. 6, the clusters are based on selections of regions that define quadrants of the visual field. FIGS. 7B to 7E define a set of 2 outer and two inner visual field ensembles or clusters of potentially active regions. FIGS. 7G to 7J illustrate an alternative set of clustered ensembles of regions where the combined quadrants are drawn from the left and right hemifields. The ensembles for FIG. 8 are based on the same rectilinear array (see FIGS. 8A and 8F), but where the regions selected to belong to a given clustered ensemble are based on every other diagonal within a quadrant of the visual field. As in FIG. 7, two alternatives based on pooling into ensembles quadrants from that same half of the visual field, FIGS. 8B to 8E; and alternate left and right halves of the visual field, FIGS. 8G to 8J. In another non-limiting design, the sets of 4 ensembles in FIGS. 7 and 8 could be presented one after the other to the two eyes alternatively as illustrated in FIGS. 4 and 6. Thus the flow chart of FIG. 5 also describes a non-limiting design on how the sets of 4 clustered ensembles shown in FIGS. 7 and 8 could be used to implement the clustered-volley design. Notice that due to the stimulus regions being selected for inclusion in a given clustered-volley being selected from alternative rows that the FIGS. 8B to 8E are nearly spatial sparse, by virtue of $p_{pair}$ mostly being $0.5*p^2_{single}$ except occasionally when adjacent stimuli appear by chance on either side of the horizontal meridian (one example each in FIGS. 8C to 8D). Due to the selected quadrants being on opposite sides of the vertical midline in FIGS. 8G to 8J, no stimuli appear adjacent to each other across the horizontal midline. Also some stimulus regions on the boundaries of a cluster have no neighbours beyond the border and so on average $p_{pair} < 0.5*p^2_{single}$. This would permit a method and device that combined the clustered-volley method and the spatially-sparse method.

In a particular non-limiting arrangement of the apparatus, a computer system 19 was used to generate stimulus sequences wherein stimuli at particular stimulus regions 31 (for example see FIGS. 3, 4, 6, 7 and 8) in the particular sequence are transmitted to LCD displays 12a and 12b by respective communication tines 11a and 11b for display to the subjects respective eyes 10a and 10b. In preferred arrangements, the sequence of stimuli displayed on each of the LCD displays is generated independently of each other such that each eye of the subject/patient is tested independently of the other eye (i.e. dichoptic stimulation). Alternatively one may wish to implement a binocular test in which case stimulus regions presented at the same positions in the visual fields of the two eyes would be presented simultaneously. Alternatively both dichoptic and binocular stimuli could be interleaved so that both types of visual field could be tested concurrently. Notice that the stimulation of the two sensory fields, i.e. the visual fields, of the two eyes demonstrates that the methods and systems described here are not limited to a single sensory field, and that the sensory fields concurrently tested may be of different sensory modalities. The computer system may also be adapted to record and fit a circle to the lower ¾ (i.e. about 75% or in the range of about 65% to 85%) of pupils with diameters larger than about 3 to 4 mm, thereby providing a measure of the pupil diameters of each of the patient's eyes independently in real time and optionally also to estimate the responses of the retina of each eye to each of the independently modulated stimulus regions that are presented to the two eyes 10a and 10b during a particular test. The lower ¾ of larger pupils is fitted to a circle because some persons, especially older persons display ptosis, or droopy upper eye lids which can obscure the pupil. For very small pupil sizes fitting the whole pupil may be advantageous given that the upper eye lids would be unlikely to obscure a smaller pupil. The stimulus sequences may be in the form of video signals displayed on the respective LCD displays 12a and 12b, which may be advantageously presented at 60 frames per second. In the present examples, the detectors 18 and 19 sampled the responses of the pupils of each of the subjects' eyes independently at a rate of 30 frames per second. In the present examples, the sampling of the pupillary responses of the patient by the detectors 18 and 19 was synchronised with every second frame of the stimulus sequence frames displayed on the LCD displays. As described above, each of the subject's pupils receives pooled input from the retina of both eyes in the form of both direct and consensual responses. Hence the pupil contraction recorded by the detectors 16a and 16b provides information about both the direct and consensual responses for each retina.

Figure 9:
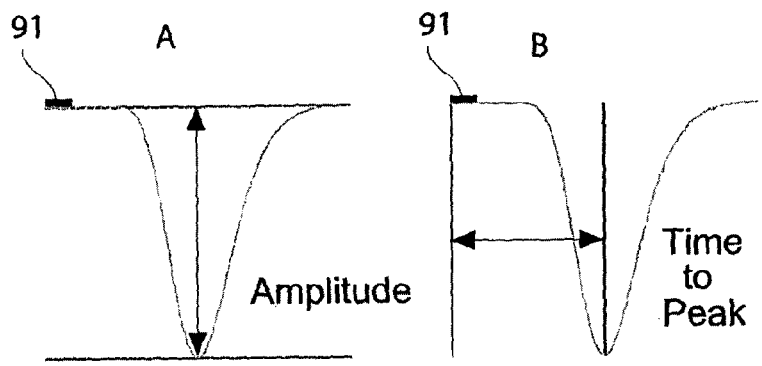
FIG. 9 are plots illustrating the form of two pupillary response waveforms as pupillary response waveform evolve in time, and the waveform's peak amplitude shown in FIG. 9A, and the time to peak shown in FIG. 9B, in response to a multifocal stimulus, where the stimulus has been delivered in the period marked by the small black rectangular block at top left of each plot 91, downward deflection of the waveform indicating constriction of the pupil to a smaller diameter from baseline.

FIG. 9 shows the form of the mean response to presentations at a single stimulus region. In each of the two panels of plots of FIG. 9A, 9B the horizontal axis represents 1 second of time following the onset of the stimulus. Each of the two example response waveforms is a downward deflecting curve that returns to baseline, where down indicates reduction in pupil diameter. The two response waveforms thus each represent a contraction of the pupil diameter followed by re-dilation to a steady state diameter. The stimulus onset and duration is illustrated by the small black rectangles 91. A key feature is the peak pupil constriction and its two related measures illustrated by the two plots: the amplitude of the peak constriction shown in FIG. 9A, and the time to peak shown in FIG. 9B.

Figure 10:
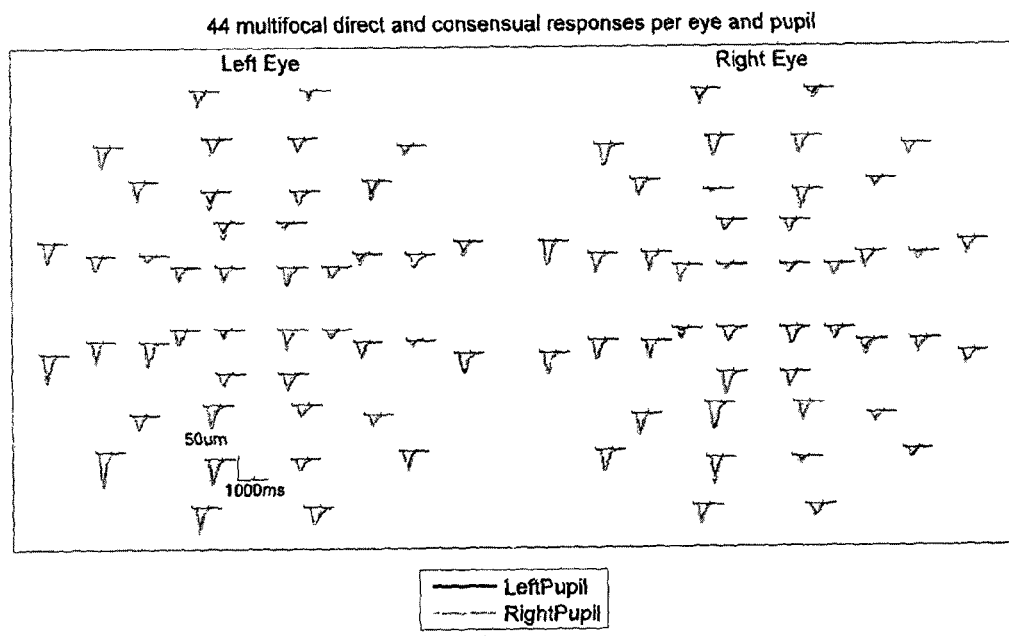
FIG. 10 shows the pairs of 44 pupillary response waveforms per eye in response to independent arrays of 44 region per eye stimuli of FIG. 3, 4, 6 presented as in FIG. 2, the black and grey waveforms being the responses recorded from the left and right pupils there being a direct and consensual response to each stimulus, and because the responses derived from each pupil are very similar the responses cause the grey response waveforms of the left pupil to frequently obscure the black response waveforms of the right pupil, thus when only the grey waveform is visible the responses from the two pupils are identical.

As described for FIGS. 1A and 1B the connectivity of the pupillary nervous system means that each pupil provides information about the activity on both retinas. Recording the activity of the two pupils means that there are two responses to each stimulus region one from each stimulus region. FIG. 10 shows the resulting collection of 176 responses from a test subject for dichoptically presented stimuli with the 44-region layout of FIGS. 3, 4 and 6. The grey waveforms are responses recorded from, the responses of the right pupil and the black for responses recorded from the left pupil. The waveforms from the two pupils are very similar and so are often completely overlapping making it difficult to see the underlying black waveform.

Pupillary Response and Pooled Gain Control

Figure 11:
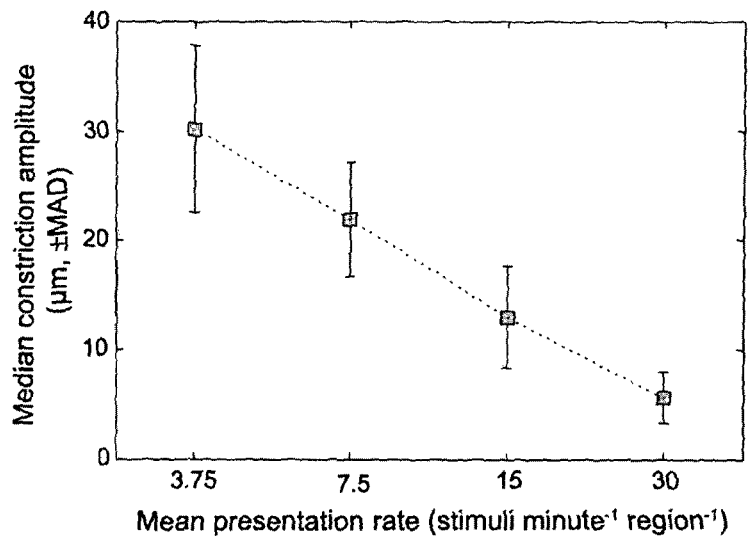
FIG. 11 is a plot illustrating the operation of a gain-control mechanism within the pupillary responses system showing that as the number of individual stimuli per second presented to regions of the visual fields of a subject increase the median peak pupillary response amplitudes decline, potentially limiting the ability of multifocal methods to assess many parts of the visual field concurrently.

FIG. 11 shows a particular feature of the responses to multifocal stimuli by the pupillary system discovered by the inventors, a particular gain control mechanism. The figure shows the result of presenting different temporal densities of multifocal stimuli. The stimuli had the 44 region layout of FIG. 3 and the older sparse multifocal stimulus method. There 4 stimulus types tested twice in the same healthy subject. The four stimulus types varied in terms of the mean interval between stimuli expressed on the abscissa as the mean presentation rate in presentations per minute per region. To make a fair comparison, each of the 4 stimuli contained 60 presentations at each region; hence, the faster stimuli were completed in less time. The ordinate is given as the median, computed across the 44 regions, 2 pupils, 2 eyes and 2 repeats, of the peak pupil constriction amplitudes 91 in micrometers±the mean absolute deviation (MAD) for each of the stimulus types. Clearly, as the stimulus density increases, the median response size drops, suggestive of a gain control mechanism.

Figure 12:
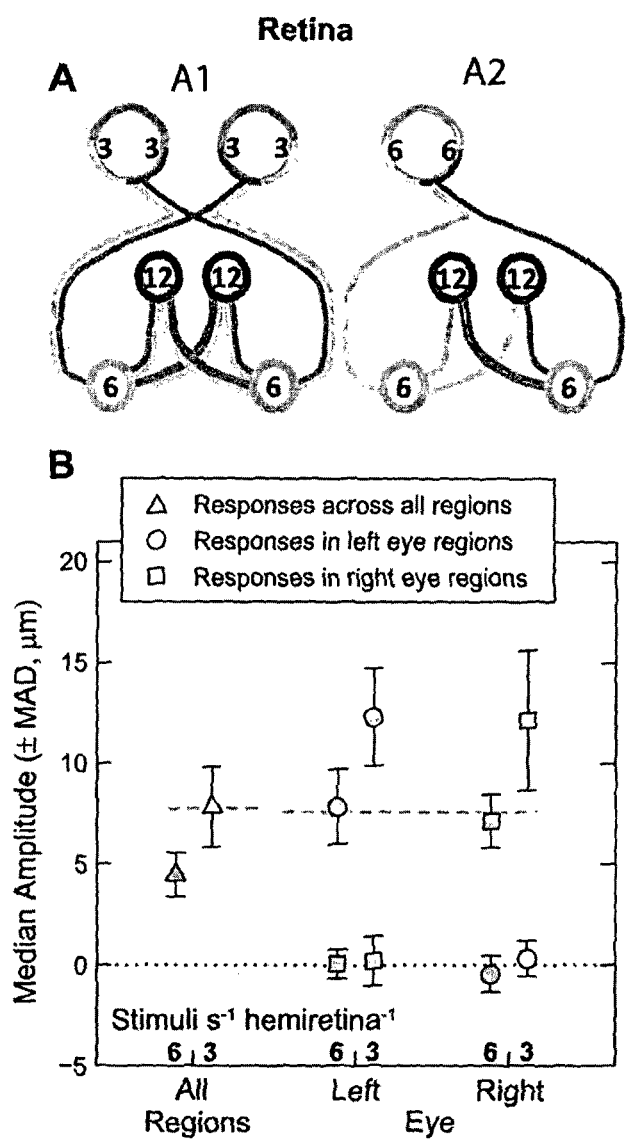
FIG. 12B shows a graph indicating that the strength of responses depends on the number of stimuli per second impinging on the EWN as illustrated by FIG. 12A, the points along the dashed lines representing different numbers of stimuli per hemiretina but the same number per EWN, and alternatively cases where the EWN received more stimuli resulting in smaller responses, or cases where the EWN receive fewer stimuli resulting in larger responses, thus isolating the point of action of the gain control to the EWN or a point after that in the pupillary pathways.

An issue is where in the pupillary pathways does the gain control operate? FIG. 12 illustrates the outcome of a set of experiments that employed clustered-volley multifocal stimuli similar to those of FIGS. 4, 5 and 6, but where typically only subsets of the hemifield clusters, or only one eye, were used and the mean presentation rate was also manipulated. Due to the structure of the visual pathways shown in FIGS. 1A and 1B, the types of manipulations of the stimuli mean that the number of stimuli per minute received by an eye, a PON or the EWN can be separately controlled. The result of experiments was that only the density of stimuli received at the EWN determined the strength of the gain control, i.e. the degree to which higher densities of stimuli reduced the median response. FIG. 12A uses the diagrammatic format of the FIG. 1B to illustrate two stimulus conditions that both result in 12 stimuli per second arriving at the EWN. The left half of FIG. 12A shows that by presentation of a mean of 3 stimuli per second to the left and right hemifields of each eye (see FIG. 12A1) that 6 stimuli per second arrive at each PON and 12 per second at each EWN. The right half of FIG. 12A shows that by doubling the presentation rate per hemifield, but only presenting stimuli to the left eye (see FIG. 12A2) that the same stimulus rate is presented to the two EWNs. Thus, if the gain control operated in the retina then one would expect that the response at each region of the stimulated hemifields would be less for the arrangement of FIG. 12A1 than for FIG. 12A2. On the other hand if the responses were the same size then one would expect an influence at the PON or the EWN. FIG. 12B shows a summary of six such experiments on 7 healthy subjects (3 males). The experiments were done in a randomised order. The three basic conditions are illustrated by the three sets of text labels below the abscissa where, from left to right, all regions (hemifields) were stimulated, only hemifields of the left eye were stimulated, or only hemifields of the right eye were stimulated. The pairs of numerals above the three abscissa markers illustrate the two alternative rates of stimuli delivered to each of the stimulated hemiretinas, either 3 or 6 stimuli per second per hemiretina. As in FIG. 11 the ordinate axis is the achieved median response amplitude. The light grey symbols indicate experiments where 3 stimuli per second per hemiretina were delivered, and the black symbols experiments where 6 stimuli per second per hemiretina were delivered. The three symbols indicating median response amplitudes of about 9 micrometers are demarked by horizontal dashed lines, indicating cases where each EWN received 12 per second all indicating that the gain control is likely to operate at the level or afterwards on the path to the pupil. Other related experiments ruled out the PONs as the site of the gain control.

Figure 13:
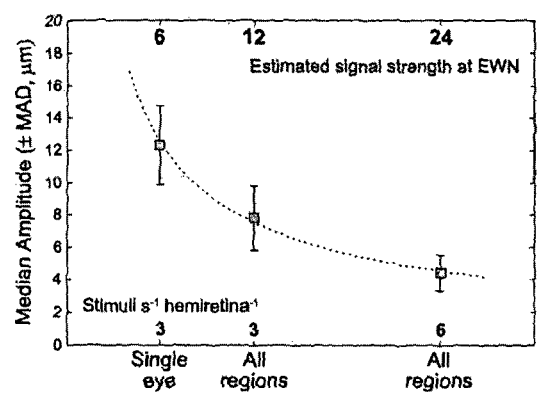
FIG. 13 is a plot illustrating the data from several experiments like those of FIG. 12B where particular numbers of stimuli per second are delivered to a particular EWN illustrating the decline in responses produced by a gain control mechanism at the EWN or afterwards on the path to the pupil.

FIG. 13 pools the data from FIG. 12. The lower abscissa labels are as in FIG. 12 and the upper abscissa labels indicate the mean rate of arrival of stimuli at the EWN. The graph shows that the median response is roughly proportional to the inverse of the number of stimuli arriving at the EWN per unit time. That is the response gain is roughly inversely proportional to the stimulus strength.

Example 1—Improved Signal to Noise Ratios in Normal Subjects

International (PCT) Patent Publication No. WO/2005/051193 describes the spatially-sparse multifocal stimulus type. The concept disclosed in that document is that there are gain controls operating within retinotopic parts of the visual nervous system. Most of the sensory parts of the brain are laid out on a sheet of neural tissue which is often folded to fit within the skull forming the familiar gyri and sulci of the human brain. A sensory part of the brain with a retinotopic representation contains a sensory brain a map of the visual field across its surface. Other sorts of sensory fields are also mapped onto different parts of the brain sheet. Within such representations there is the possibility of gain controls can operate that interact at short ranges across the sheet. The retinotopic mapping means that means the gain controls can affect responses to stimulation of adjacent parts of the visual field. International (PCT) Patent Publication No. WO/2005/051193 showed that when measuring visual evoked potentials from the occipital visual cortex in response to multifocal stimulus arrays presented across the visual field, that such regional gain controls operate. Accordingly, International (PCT) Patent Publication No. WO/2005/051193 taught that multifocal stimulus sequences should be restricted such that when a stimulus is presented at one small region of the visual stimuli others should not be presented at the same time at spatially adjacent locations, hence the stimuli of International (PCT) Patent Publication. No. WO/2005/051193 are referred to as being spatially-sparse.

The EWN is an example of a brain region that is not very retinotopic in its representation of the visual world. Therefore one might expect that spatially-sparse stimuli might not provide much of an advantage. In the course of investigating location of the gain control of FIGS. 11, 12 and 13 the inventors realised that clustered-volley stimuli used in those experiments appeared to be giving responses that were larger, and which had larger signal to noise ratios, than the sparse stimuli that had been investigated before. This was a surprising discovery because, as shown in FIG. 6, the stimuli were clearly not spatially-sparse. Indeed, presenting the stimuli in clusters to restricted portions of the visual field seemed to provide an additional benefit. To prove that point, the inventors undertook a series of experiments where spatially-sparse and clustered-volley multifocal having the same mean presentation rates were compared head to head in the same persons. Notice that this admits the possibility that other brain areas that do not have a strong topographic map of sensory space might also benefit from multifocal clustered-volley stimuli being applied to their sensory space.

Figure 14:
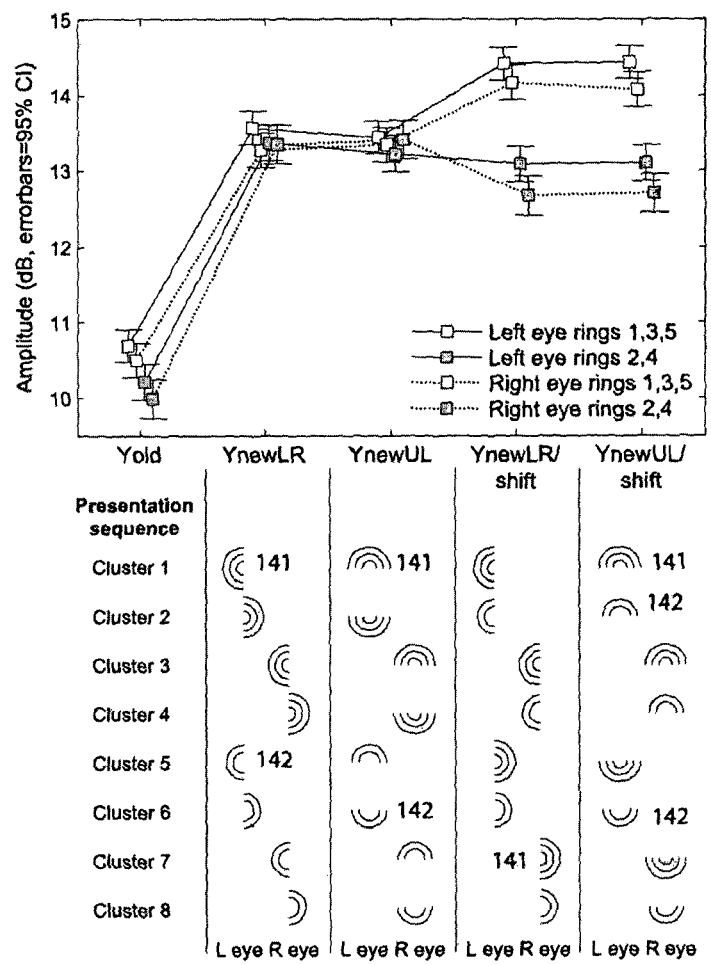
FIG. 14 shows a comparison between mean per region pupillary responses obtained for the previous spatially-sparse method of International (PCT) Patent. Publication No. WO/2005/051193, the data for that stimulus type is shown above the abscissa label Yold, and four clustered-volley stimulus variants related to those in FIGS. 5 and 6 but where the order and orientation of the hemifield ensemble cluster is varied across the 4 alternative non-limiting designs, showing mean per region responses for the different stimulus rings of FIG. 3, showing for all clustered-volley variants the responses are significantly larger given that the error bars are the 95% confidence limits.

FIG. 14 illustrates results from 5 such experiments on 6 normal persons (3 males) where each of the 5 experiments was repeated. The experiments were done in a randomised order. The stimuli were yellow and had a maximum luminance in their active state of 144 cd/m$^2$ presented on a yellow background inactive state of 10 cd/m$^2$. All five stimulus types presented stimuli controlled by pseudorandom sequences that produced a mean stimulus interval of 4 seconds. The results from the five experiments are summarised across the 5 points of the abscissa. The first (leftmost) point for FIG. 14 represents data from a spatially-sparse method, labelled Yold on the abscissa. The other four abscissa points indicate data from 4 types of clustered-volley stimuli. The four stimulus types were as described by FIGS. 4, 5, and 6 except that either the orientation or presentation order of the stimuli presented to each was possibly varied. The hemifield ensembles, or clusters, drawn from the three rings of FIG. 3A are represented by three nested half-circles 141 and those drawn from the two rings of FIG. 3B are represented by two nested half-circles 142. To avoid clutter, not all the set of two and three nested rings are labelled 141 and 142. The rings thus refer to the groups of rings of stimulus regions shown in FIGS. 3A and 3B, and also shown in FIGS. 4 and 6. The sequences of clustered half rings of stimulus regions are illustrated below each of the four rightmost abscissa points. The abscissa labels include reference to HR and UL indicating that the hemifields were created from left and right quadrants of the visual field (YnewLR) and upper and lower quadrants (YnewUL), which is evident from the plotted rings below the respective abscissa labels. Those plotted rings illustrate the hemifields clusters that are interleaved in the round robin presentation much as in FIGS. 4, 5, and 6. The data points shown are the output of a linear model where the peak pupil constriction data were transformed to decibels. The linear model computed separate means for each eye and for each of the clustered-volleys from rings 1, 3, 5 or 2, 4 as indicated by the legend of FIG. 14. Obviously, all the clustered-volley methods produce larger responses that the Yold spatially-sparse method for all rings and both eyes. Surprisingly, the use of upper and lower versus left and right hemifields ensembles seems to make no difference. Notice the first of the clustered-volley stimuli, labelled YnewLR on the abscissa, is the same stimulus method as illustrated in FIGS. 4 and 6, and those cases in FIG. 12 where all hemifields were stimulated. The second clustered-volley stimulus type, labelled YnewUL, only differed by the hemifield clusters being defined for the upper and lower visual field. A second linear model was created pooling the responses across eyes and rings the comparison of the responses for the spatially-spare stimuli and these first two clustered-volley types the results are shown in Table 1. The significance of the differences between the spatially-sparse and clustered-volley stimuli were significant at $p<2.3\times10^{-8}$. These results were based on taking the medians across regions, eyes and pupils before the data were entered into the model and so are fully Bonferroni corrected for repeated measures. Another possible interpretation of the improvement seen for YnewLR and YnewUL is that given the lack of stimuli that overlap in the same field location within a short time, this might reduce spurious accommodative near-responses of the pupils to what the brain might interpret as stereoscopic depth cues.

TABLE 1

| Stimulus type | Peak Amplitude (decibels) | SE |
| --- | --- | --- |
| Yold | 10.1 | 0.37 |
| YnewLR | 13.6 | 0.53 |
| YnewUL | 13.5 | 0.53 |

The rightmost two data sets of FIG. 14, positioned above abscissa labels YnewLR/Shift and YnewUL/Shift, represent the mean data for two further variations of the clustered-volley stimulus type. These were the same as YnewLR and YnewUL except that the presentation order within the round robin sequence is permuted such that ring 1, 3, 5 stimuli are followed by ring 2, 4 stimuli presented to the same hemifields of the same eyes. This difference is indicated by the figures below each abscissa label. This means that stimuli occurring in as little as 0.25 seconds may follow each other for those hemifields. This seems to suppress responses to the ring 2, 4 stimuli and enhance the responses to the 1, 3, 5 stimuli. The enhancement is presumably caused by the ring 1, 3, 5 stimuli now arriving further apart in each cycle.

Figure 15:
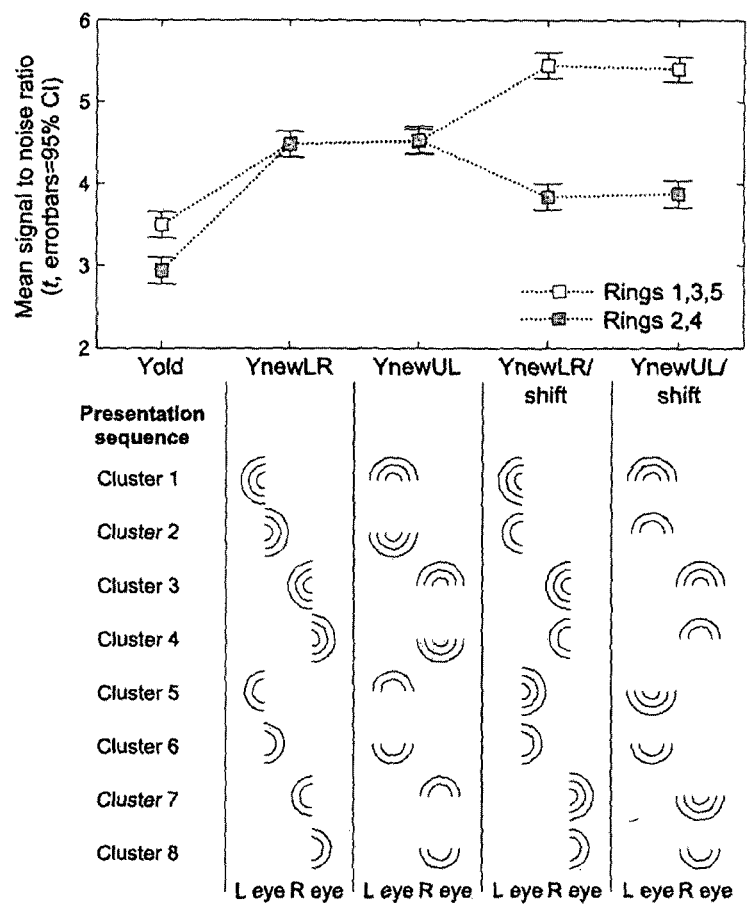
FIG. 15 shows comparisons between the signal to noise ratios obtained in the experiment of FIG. 14 (SNRs) obtained where the SNRs are computed as means across eyes and subjects leaving separate results to the two clusters of rings, showing as in FIG. 14 that SNRs for the four new variants are significantly higher than for the older spatially-sparse method, all five stimulus types having the same 44 yellow regions as in FIGS. 3, 4, and 6 and the same mean presentation interval of 4 seconds/region.

FIG. 15B is similar to FIG. 14 but the plotted data are the mean signal to noise ratios (SNRs) achieved. Each of the peak pupil constriction points comes with a standard error (SE) estimating the reliability of that peak. This permits the SNRs to be quantified as a t-statistic estimated as peak response divided by its SE. This gives an indication of the confidence that the measured peak is not 0. In FIG. 15B, the linear model computed means across eyes leaving only results for the ensembles of rings. The clustered-volley stimuli all produce better SNRs than the spatially-sparse method. The result for the permuted clustered-volley stimuli are also similar with the 1, 3, 5 rings producing t-statistics over 5. This suggests that these stimuli could be preferentially used if used rings 1, 3, 5 were of particular interest, or alternatively some other cluster could be selected for enhanced SNR. A linear model pooling responses across eyes and rings like that of Table 1 was created and is presented as Table 2. Unlike the peak amplitudes, the t-statistics did not require log-transformation but the same averaging to prevent any issue of repeated measures was applied. The significance of the differences between the spatially-sparse and clustered-volley stimuli were significant at $p<1.5\times10^{-7}$.

TABLE 2

| Stimulus type | SNR (t-statistic) | SE |
|---|---|---|
| Yold | 2.78 | 0.19 |
| YnewLR | 4.47 | 0.27 |
| YnewUL | 4.41 | 0.27 |

These results suggested that surprisingly the clustered-volley method was better than the spatially-sparse method. That is to say that presenting the stimuli in clusters produced better performance that dispersing the stimuli diffusely across the visual field. This also suggested that the EWN gain control involved a feed-back mechanism that was too slow to dampen down the stimuli when the stimuli were delivered in volleys. Alternatively, the gain control may summate over the whole visual field in some piece-wise fashion such that delivering volleys to parts of the visual field about the size of a quadrant or two does not provide as strong a signal to the gain control mechanism as presenting stimuli at the same rate across the whole field.

Figure 16:
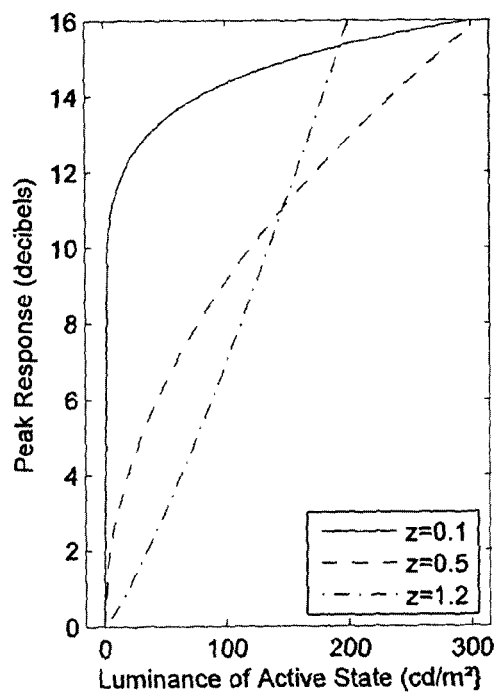
FIG. 16 shows the potentially saturating form of stimulus versus response functions (SRFs) that are modelled as power functions of the form Response=k×(Contrast)$^z$ where values of the exponent $z \ll 1$ lead to SRFs that plateau, i.e. the SRFs saturate, in response to higher luminance contrast, the background contrast here being assumed to be about 10 cd/m$^2$.

The larger responses on their own may be a problem for some applications if the responses produce functions relating response magnitude or signal to noise ratio to stimulus strength that saturate. Such functions are often called stimulus response functions (SRFs). FIG. 16 illustrates the problem showing hypothetical SRFs with the form of a power function: Response=k×Contrast$^z$. Here contrast is calculated as (test luminance/background luminance)−1. To aid understanding FIG. 16 is plotted not with contrast on the abscissa but the test luminance. Three SRFs are shown whose shape is defined by three different exponents. The solid SRF is for the plot with the smallest exponent, z=0.1. The curve rises rapidly with increasing stimulus luminance but then begins to plateau or saturate. The problem for some applications is that the saturating curve means that if one were attempting to use small reductions in response to indicate damage to a part of the visual field, then the saturation would tend to make responses from damaged and undamaged, or super normal, visual field regions similar. Given that the clustered-volley method makes responses larger, it is important to demonstrate that the clustered-volley method does not also cause strongly saturating stimulus response functions. Alternatively stimulus strengths should be determined that provide adequate responses but that are not so large as to be affected by any saturation.

To examine whether clustered-volley stimuli produce overly saturating SRFs a group of six normal subjects (3 males) was tested with three different stimulus types. In their active state, these three types were presented stimulus regions that had maximal luminances of 37.5, 75, 150 or 300 cd/m$^2$, making 12 stimulus types. The 12 types were tested in randomised order. Two of the stimuli were first two stimuli of FIGS. 14 and 15, Yold and Ynew (YnewLR in FIGS. 14 and 15), making the clustered-volley stimulus the same as that of FIGS. 4, and 6. The third type was the same in all aspects to the Ynew stimulus except the third type presented green stimuli on a red background, and the type is referred to as RGnew. That is to say, depending on the test, the active state was green at 37.5, 75, 150 or 300 cd/m$^2$, and the inactive state was equal to the background red at 10 cd/m$^2$. As in FIGS. 4 and 6, the stimulus array of 44 regions covered the central 60 degrees of the visual field.

FIG. 17A shows the resulting median responses, computed across subjects, stimulus regions, eyes and pupils, and the error bars are SE for the three stimulus types as indicated by the legend. None of the SRFs is heavily saturated, however the SRF for the Ynew stimulus suggests that stimulus luminances much above 200 cd/m$^2$ might be ill advised. The signal to noise ratios of FIG. 17B appear to show somewhat less saturation. A linear model of the t-statistics results for the data for 150 cd/m$^2$ showed results very similar to those of Table 2. The improvements in the SNRs for Ynew and RGnew relative to Yold were significant at $p<0.005$. The analyses were repeated for the other three active luminance levels and the results were similar.

TABLE 3

| Stimulus type | SNR (t-statistic) | SE |
|---|---|---|
| Yold | 3.38 | 0.25 |
| Ynew | 4.30 | 0.31 |
| RGnew | 4.36 | 0.31 |

Figure 17:
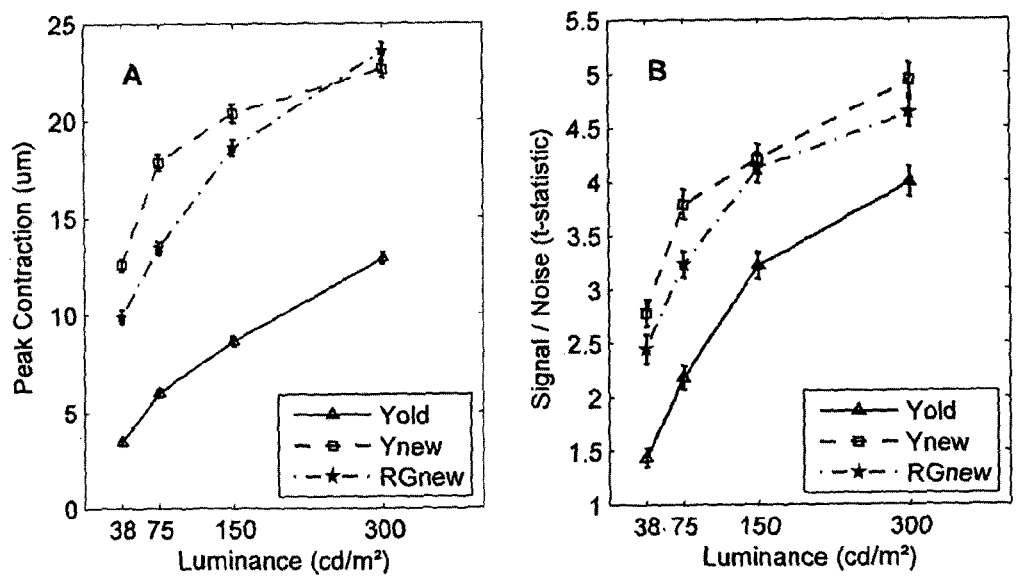
FIG. 17 shows measured SRFs from six subjects showing that both the older spatially-sparse (Yold) and newer clustered-volley stimuli (Ynew, RGnew) show fairly unsaturated response forms, and this is true for both the peak pupillary response amplitudes in FIG. 17A and the signal to noise ratios FIG. 17B.
Figure 18:
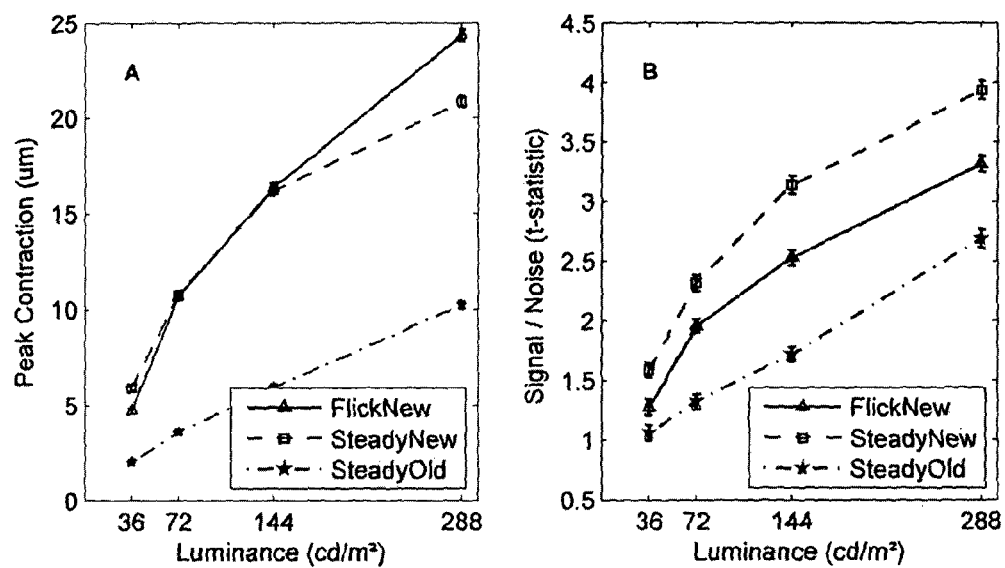
FIG. 18 is similar to FIG. 17 except that unlike that figure the stimulus arrays did not cover the central 60 degrees of the visual field but were reduced in scale isomorphically to stimulate only the central 30 degrees of the visual field and the SRFs were measured for 18 young normal people, none of whom were measured for FIG. 17.

The results summarised in FIG. 17 and Table 3 were compelling, but were based on relatively few subjects and some of the same subjects were shared between that study and the one of Tables 1 and 2. Therefore, a larger study was done on new subjects. Like the previous study, there were three basic stimulus types but the types differed in one fundamental way from all the stimuli described thus far, all three stimuli were isomorphically reduced in scale relative to those illustrated in FIG. 3 such that the 44 stimulus regions occupied only the central 30 degrees, rather than the central 60 degrees. The 60 degree arrays of stimuli like those described to this point are designed to assess visual function in the peripheral visual field, while the small 30 degree array is directed at assessing function in the central visual field corresponding roughly to the macula of the retina. All the stimuli were yellow presented on a background of 10 cd/m². The first stimulus, referred to as SteadyOld, was a spatially-sparse stimulus like Yold and like all the stimuli presented so far were presented in an active state for 33 milliseconds as described as T1 in FIG. 5. The second stimulus, referred to as SteadyNew was a clustered-volley stimulus like Ynew and described in FIGS. 4, 5 and 6 except for its reduced spatial scale, and also displayed stimuli in their active state for 33 milliseconds. The third stimulus type, referred to as FlickNew was a clustered-volley stimulus of the type that was temporally exactly like SteadyNew except that it presented stimuli that flickered during the active period T1. This flickering active state showed the active luminance for 33 ms, the inactive luminance of 10 cd/m² for 33 ms, and then the active luminance for 33 ms, before returning to the inactive state. This type of flicker, is sometimes referred to as pedestal flicker because the mean luminance during the flicker is larger than the background. Pedestal flicker has been used in some studies of eye disease and is thought to be an effective stimulus for some such applications. All the stimuli had a mean presentation interval of 4 s/region. These three stimulus types were presented at 4 luminance levels, of 36, 72, 144, or 288 cd/m². Eighteen subjects, 9 males, with a mean age (±SD) of 21±0.97 years were invested and given a thorough eye exam to determine that the subjects were normal. Six of the subjects were Asian and the remainder Caucasian. The stimuli were presented in a randomised order over three visits by each subject. In fact there were 9 random orderings of the stimuli, which were assigned at random to 9 subjects, and the remaining 9 subjects completed the tests in the reverse orderings to insure a well-balanced statistical design. Half the stimuli, i.e. six, were completed on 1 prototype device of the type described in FIG. 2, and the other six on a second device that was designed to be identical to the first. The order of testing on the two devices was randomised. The inventors also took note of the subjects' dominant hand and dominant eye. FIG. 18 is similar to FIG. 17 and presents the median SRFs for the three stimulus types as indicated by the legend.

A linear model examined all the various factors mentioned that might determine components of the mean signal to noise ratios expressed as a t-statistic as in Tables 2 and 3. The SRFs of FIG. 18 were somewhat less saturating than those of FIG. 17 and therefore the linear model examined was based on the results obtained at 288 cd/m². The significant results ($p<0.001$) are shown in Table 4. The factors: visit, gender, device, dominant hand or dominant eye, were not significant determinants of the SNRs. The analyses were repeated for the other three active luminance levels and the results were similar.

TABLE 4

| Stimulus type | SNR (t-statistic) | SE |
| --- | --- | --- |
| SteadyOld | 2.97 | 0.74 |
| FlickNew | 3.49 | 0.16 |
| SteadyNew | 4.13 | 0.17 |

Overall the three experiments summarised in this section indicate that relative to spatially-sparse stimuli the clustered-volley stimuli produce improved signal to noise ratios. Thus the quality of any assessment of the visual fields would be improved, or alternatives the duration of the test could be reduced to achieve an acceptable signal to noise ratio.

Example 2—Clustered-Volley Stimuli in Glaucoma

The relative diagnostic power for discriminating normal subjects from open angle glaucoma patients was investigated with the 150 cd/m² variants of the three wide-field stimuli of Table 3: Yold, Ynew and RGnew. As before all three stimulus types had mean stimulus intervals of 4 seconds per region. Subjects' diagnostic status was confirmed using FA-II achromatic perimetry (SITA-FAST), Matrix 24-2 perimetry, Heidelberg Spectralis spectral domain Optical Coherence Tomography (OCT), slit lamp bio-microscopy and applanation tonometry. Subjects had to pass the manufacturers criteria on false positives, negatives and fixation losses on the perimetry. Exclusion criteria for all subjects included acuity worse than 6/12, distance refraction of more than ±6 dioptres, or more than 2 dioptres of cylinder. Normal subjects had no primary relatives with glaucoma. The study group included 24 normal controls and 22 OAG patients. The normal controls and patients were age and sex matched, and were each tested twice with all three multifocal methods about 2 weeks apart. Table 5 summarises the subject parameters. The eyes of the patients were segregated into 3 severity groups on the basis of the mean defect (MD) from the HFA perimeter tests: mild eyes had MD>−6 dB, moderate eyes MD≤−6 dB and MD>−12 dB, and severe eyes MD<−12 dB.

TABLE 5

| Subject group | N subjects | N males | Age ± SD years |
| --- | --- | --- | --- |
| normal | 24 | 12 | 66.0 ± 8.59 |
| glaucoma | 22 | 15 | 64.8 ± 9.15 |

Linear models were constructed to compare the signal to noise ratios obtained in the normal subjects for the three stimulus types. As a correction for multiple measurements the inputs to the model were the mean t-statics computed across pupils, eyes and stimulus regions to produce a single number for each of the 24 normal control subjects. The outcomes are presented in Table 6 and despite the study group being older than for Table 3 the results were remarkably similar. The improvements in mean SNR for Ynew and RGnew relative to Yold shown in Table 6 were significant at $p<6\times10^{-6}$.

TABLE 6

| Stimulus type | SNR (t-statistic) | SE |
| --- | --- | --- |
| Yold | 3.22 | 0.16 |
| Ynew | 4.30 | 0.19 |
| RGnew | 4.08 | 0.19 |

Figure 21:
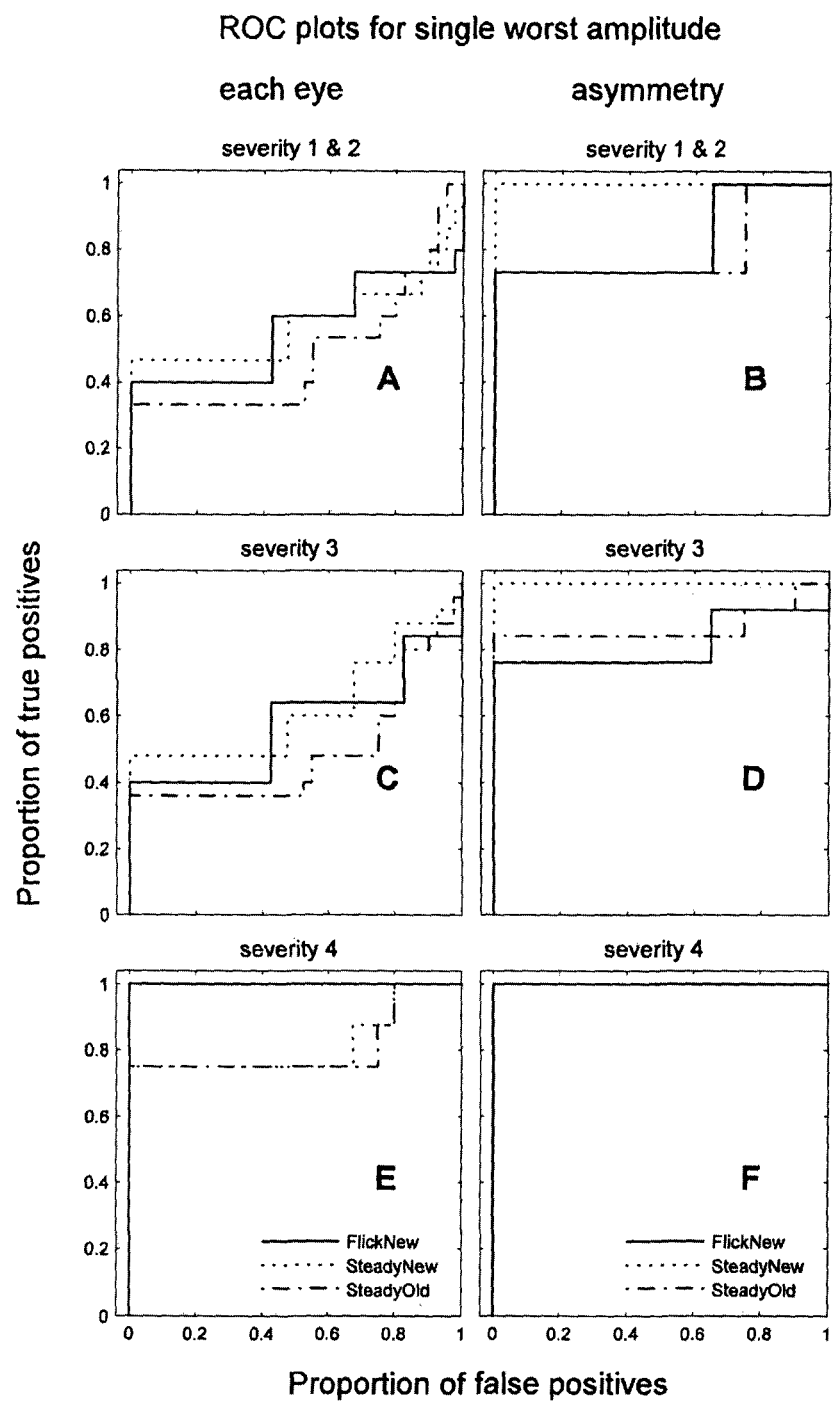
FIG. 21 shows Receiver Operator Characteristic (ROC) plots indicating the diagnostic power of an older spatially-sparse stimulus type versus (SteadyOld) and two clustered-volley stimulus types (FlickNew and SteadyNew) for 3 AMD severity levels and comparing each eye against normative data or comparing asymmetries in pupil response amplitude between each subjects' eyes.

Diagnostic power was quantified as the percentage area under curve (AUC) of receiver operator characteristic plots (ROC). As shown in FIG. 21 ROC plots show the true positive rate for diagnosing patients on the ordinate, and the false positive rate for mis-diagnosing normal control subjects on the abscissa. Perfect performance, all patients diagnosed correctly and no normal controls mis-diagnosed, is indicated by an AUC of 100%. Chance diagnostic performance is indicated by an AUC value of 50%. The ROC analysis was based upon the deviations of regions of each measured visual field from a normative reference visual field derived from the pupillary responses at each of the 44 regions of the normal control subjects. The differences between the 44 values of the reference field and the 44 values from each eye of each subject were computed and are referred to as the deviations from normal. The deviations were converted to decibels (10 $\log_{10}$) and then to z-scores of a normal distribution.

Figure 19:
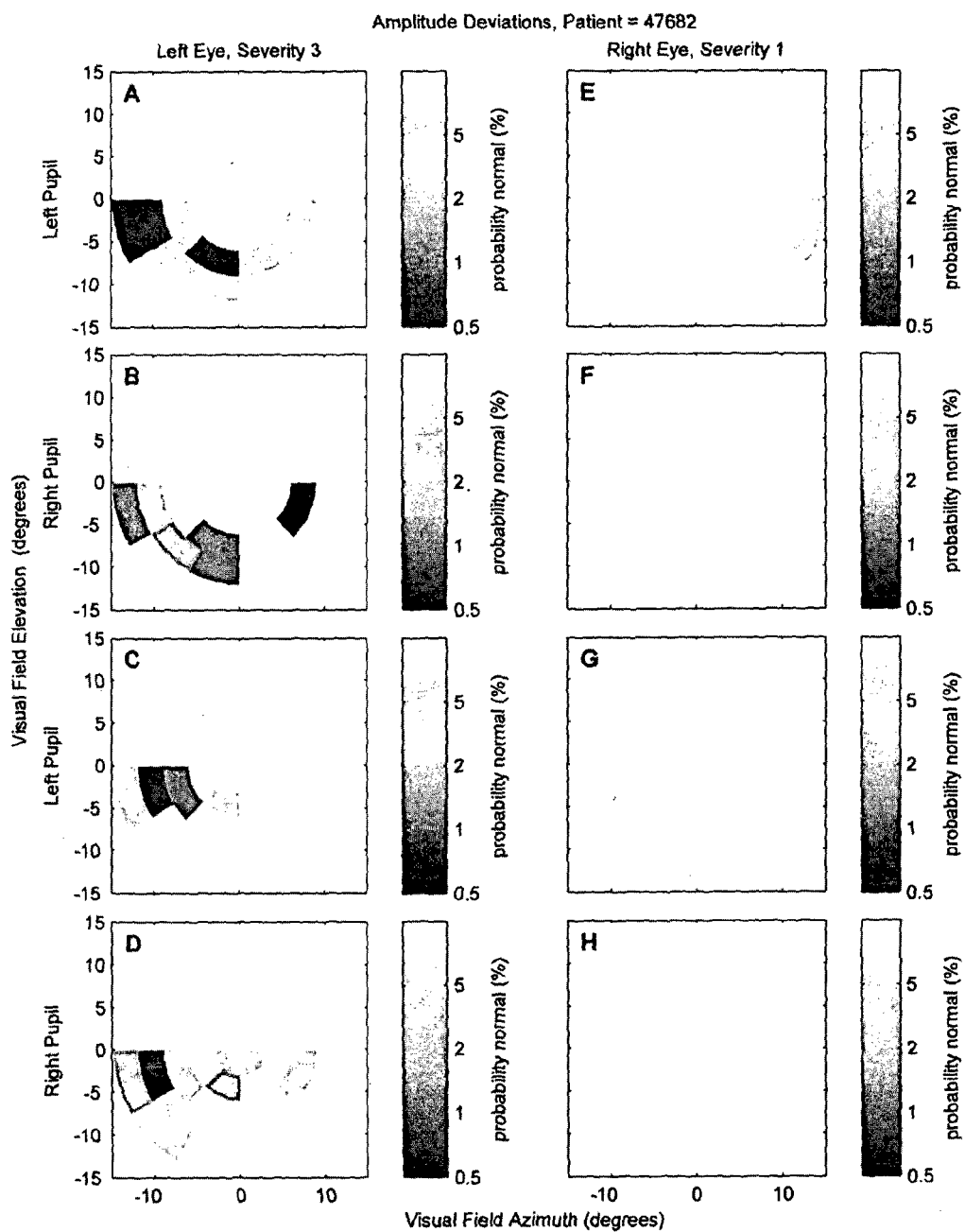
FIG. 19 shows the deviations from normal control eyes of the peak pupil constriction amplitude measured using the Ynew clustered-volley stimulus type from the eyes of a glaucoma patient transformed into percentage probabilities that a given visual field region is normal as expressed by the darkness of the coloring of each region, where the data for left eye is in the left column (FIGS. 19A, 19B, 19C, 19D) and the right eye in the right column (FIGS. 19E, 19F, 19G, 19H) and the rows of figures are for the subject's left and right pupil, with data presented for a first test in FIGS. 19A, 19B, 19E, 19F, and for a second repeat test about two weeks later in FIGS. 19C, 19D, 19G, 19H.

FIG. 19 shows an example of the deviation data for the visual fields of a glaucoma subject for the Ynew stimulus method. The data are presented in a way that will be familiar to a person skilled in perimetry in which the z-score deviations have been converted to probabilities that the results obtained in at each location in the visual field are normal. The grey levels in each plot correspond to p=5, 2, 1 and 0.5% as is common in SAP, thus darker colored regions indicate a high probability that part of the visual field produces abnormally small pupillary responses. The two columns correspond to results for the left (FIG. 19A to 19D) and right eye (FIG. 19A to 19D). As indicated by the title of FIG. 19A the left eye is rated as being in severity category 3, i.e. a severely damaged eye having an HFA MD<−12 dB. The right eye is a mildly affected eye in severity category 1 having an HFA MD>−6 dB. As shown by the ordinate labels on the left column figures the rows of FIG. 19 are results from the left and right pupils. The upper four figures, FIGS. 19A, 19B, 19E, 19F, are the results obtained on the first test and the lower four figures, FIGS. 19C, 19D, 19G, 19H, are based on data obtained on the repeated test. Overall the results for each eye are quite consistent between pupils and repeats. The fact that the results follow the eye and not the pupil indicate that the damage is on the afferent pathway from the eye to the brain and not on the efferent pathway from the brain to the pupil. The results were in good agreement with other perimetry methods.

In this study, the reference visual field data for each protocol used in the ROC analyses was computed as the median value, either decibel peak amplitude or time to peak, at each visual field location measured across eyes and pupils (direct and consensual responses) of the normal controls. The ROC analysis also employed a form of cross-validation, the Leave-One-Out (LOO) strategy. In LOO the ROC analysis for each normal subject's field is repeated with that field removed from the reference data, hence the data from a given normal subject's field does not bias its own classification. Before computing the medians the fields from right-eye fields were reflected left-to-right so that naso-temporal location was in correspondence between left and right eyes. Separate ROC plots were computed comparing normal controls and each of the three glaucoma severity groups. For each of those data sets the ROC plots were done 20 times, where on each step the ROC analysis was based on worst N deviations, where N ranged from 1 to 20. Thus, ROC for N=1 the ROC plots were created for the single region of each visual field that differed most from normal (the worst point in each field). For the subsequent ROC plots mean of the worst 2 regions per visual field, the worst 3 regions and so on, the AUC value being recorded from each plot. The purpose of this was to work out the degree to which the pupillographic multifocal methods can detect localised damage. For example if the single worst point (N-worst=1) had the highest AUC value that would mean that no normal ever had a significantly damaged visual field region and even one such point in a patient's eye provided perfect diagnostic power (AUC=100%). On the other hand, if the highest AUC was only achieved for N-worst=20, that would mean that results from many regions need to be averaged to achieved reasonable diagnostic power and thus the method cannot detect the localised damage typical of glaucoma.

Figure 20:
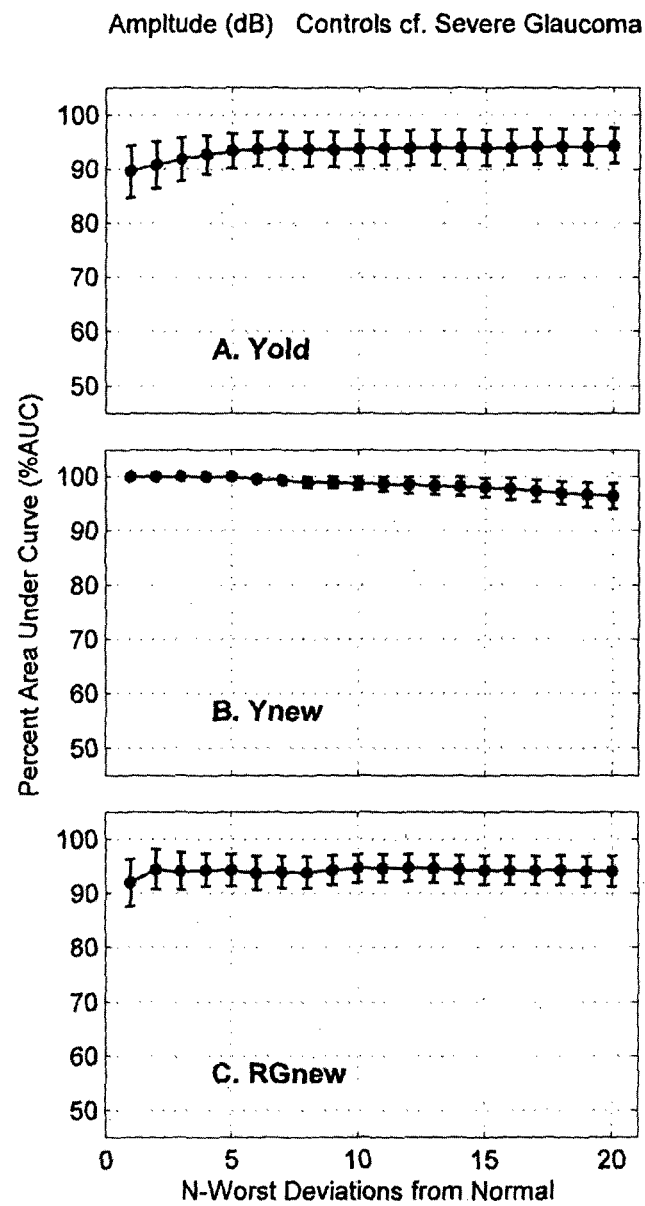
FIG. 20 comprises plots for an older spatially-sparse stimulus type versus (YOld) and two clustered-volley stimulus types (YNew and RGNew) indicating the percentage area under curves (% AUC)±SE, of ROC plots like those of FIG. 21, for diagnosing severe glaucoma when the number of the worst deviating regions in each measured visual is increased from the single most deviating region up to the worst 20 regions, where AUC=100% means all patients and normal controls are diagnosed correctly.

FIG. 20 shows plots of the percentage AUC values obtained for the first to twentieth worst performing regions of all the severely damaged eyes for the three stimulus types and the error bars indicate the standard errors (SE). FIG. 20A shows that Yold needs 5 or more points to be averaged to achieve a reasonable AUC of around 95%. FIG. 20C indicates the RGnew does better, achieving its best performance when about the worst 2 regions in the visual field are considered. FIG. 20B shows that, at least for this disease severity group, the diagnostic performance was perfect, all subjects correctly classified, with SE that are essentially 0 for between the worst 1 and 5 regions. Clearly the clustered-volley methods outperformed the older spatially sparse method diagnostically. The mean AUC values for the combination of the $1^{st}$ and $2^{nd}$ worst points in each visual field are summarised in Table 7±their standard errors. The rows of Table 7 correspond to the three severity categories. The third row, labelled "mod & sev" gives the results when the data from moderately and severely affected fields are pooled, that is for patient eyes with HFA MD<−6 dB. An interesting effect is that while the RGnew does not perform as well as Ynew for the severe eyes RGnew performed best for mild and moderately affected eyes.

TABLE 7

| HFA Severity | Yold | Ynew | RGnew |
|---|---|---|---|
| mild | 57.9 ± 6.81 | 55.6 ± 7.52 | 66.9 ± 6.91 |
| moderate | 72.0 ± 5.87 | 79.8 ± 6.15 | 86.1 ± 4.80 |
| mod & sev | 78.3 ± 4.50 | 86.8 ± 4.28 | 88.6 ± 3.53 |
| severe | 90.2 ± 4.58 | 100 ± 0.00 | 93.2 ± 4.03 |

Example 3—Clustered-Volley Stimuli in Macular Degeneration

Versions of the three macular oriented stimulus types of Table 4, that presented 44 stimulus regions to the central 30 degrees of each visual field, were used to compare the diagnostic power for detecting Age-related Macular Degeneration (AMD) of the older spatially-sparse stimuli, Steady-Old, with the two new clustered-volley stimuli. FlickNew and SteadyNew. The stimuli were yellow like those in Table 4 but had a maximum luminance of 288 $cd/m^2$ in their active, state, presented on a 10 $cd/m^2$ background. Table 8 summarises the demographics of the patients and age-matched normal control subjects. All subjects were examined as for the glaucoma study above and the exclusion criteria were similar. In addition, color retinal photographs were taken using a nonmydriatic fundus camera with a 45 degree field of view.

TABLE 8

| Subject group | N subjects | N males | Age ± SD years |
|---|---|---|---|
| normal | 19 | 8 | 70.2 ± 4.94 |
| AMD | 24 | 9 | 69.7 ± 11.6 |

Table 9 shows the results of a linear model comparing the t-statistic based signal to noise ratios achieved in the normal controls that were about 4 years older than those in Table 6. As in Table 4, the signal to noise ratios for the two clustered-volley stimuli were significantly larger that for Steady, at $p<0.04$ for FlickNew, and $p<10^{-8}$ for SteadyNew.

TABLE 9

| Stimulus type | SNR (t-statistic) | SE |
|---|---|---|
| SteadyOld | 3.34 | 0.22 |
| FlickNew | 3.76 | 0.21 |
| SteadyNew | 4.60 | 0.21 |

The methods for creating the deviations from normal for each eye were identical to those used to produce FIG. 20 and Table 7 including using the LOO method when computing the normative data. One additional method was added in which the asymmetry, i.e. the difference, between results obtained for the two eyes of each subject was computed for each of the 44 locations in the visual field. Normative data for and these asymmetry measures formed and the deviations from the normal between eye asymmetries formed the input to the ROC analyses. FIGS. 21A, 21C, 21E show ROC plots based on the deviations from normal for data based on each eye, while FIGS. 21B, 21D, 21F show the results for the asymmetry measures. As shown by the legends, there are 3 ROC plots per figure, one for each of the stimulus types: SteadyOld, FlickNew and SteadyNew. Patient eyes were segregated into AMD severity categories based on the well-known Age-Related Disease Study (AREDS) published in "The age-related eye disease study system for classifying age-related macular degeneration from stereoscopic color fundus photographs: the age-related eye disease study report number 6" by the AREDS Research Group in the *American Journal of Opthalmology*, 2001, Volume 132 (5), Pages 668-681. The AREDS standard has four disease severity levels ranging from quasi-normal to end-stage AMD. For this study, the inventors pooled eyes in the first two AREDS categories 1 and 2 to form a mild disease Category. AREDS categories 3 and 4 were equated to moderate and severe AMD. The severe category included eyes with neovascular AMD or geographic atrophy threatening the fovea. The three rows of figures of FIG. 21 correspond to the mild, moderate and severe categories. All the ROC plots are based on the single most deviating region of the field considered, whether the deviations from normality were based on each eye or the asymmetry between eyes. The dotted ROC plots of FIGS. 21B, 21D, 21F indicates that the SteadyNew stimulus achieved an AUC of 1.0 (i.e. 100%) indicating all subjects in all severity categories were correctly diagnosed while no normal controls were misdiagnosed. The result for the mild eyes is surprisingly good as no other method has achieved such results.

Figure 22:
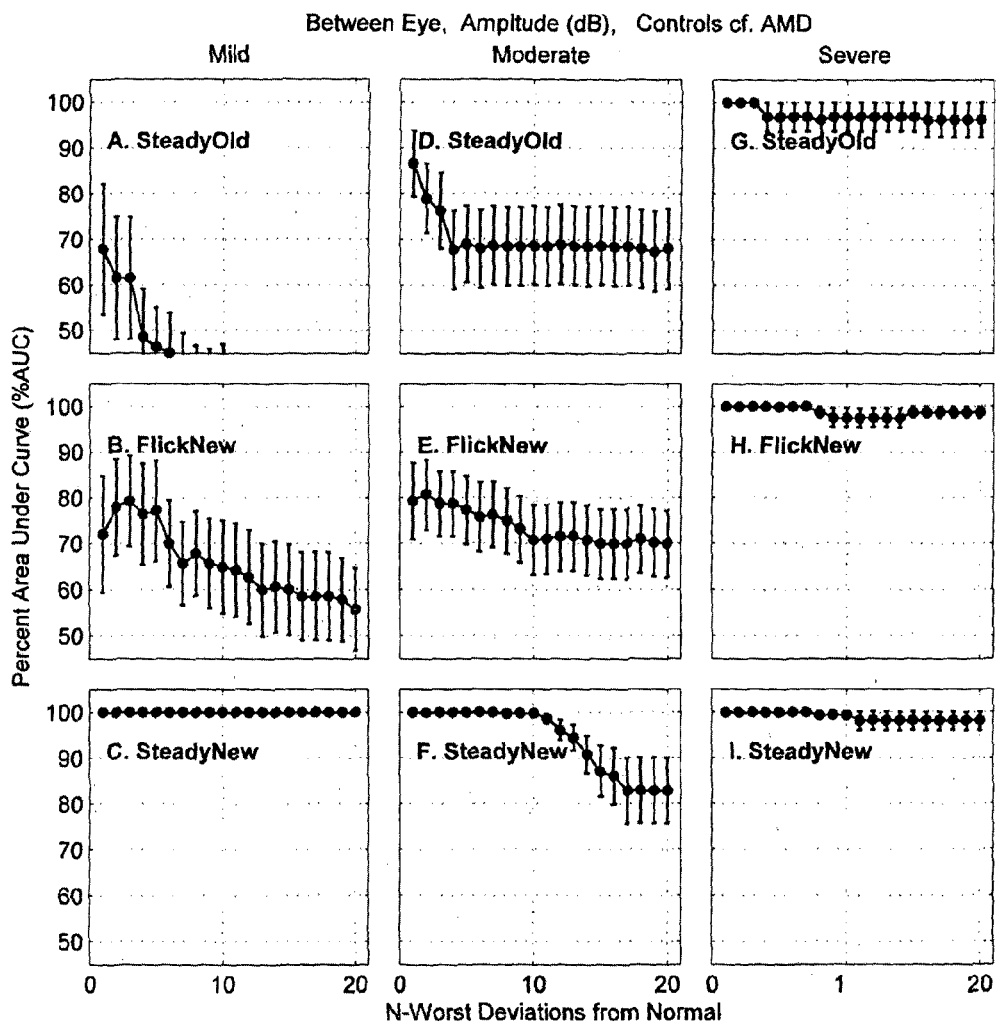
FIG. 22 is similar to FIG. 20 but the three columns of figures show plots of % AUC versus the number of N-worst regions of each visual field for three severities of AMD.

FIG. 22 is similar to FIG. 20 in showing the percentage AUC plotted as a function of the number of the worst visual field regions considered for the analysis. As in FIG. 21, and as indicated by the overall figure title, the deviations used for the ROC analysis were all based on the between eye asymmetry in the measured peak pupillary response amplitudes transformed to z-scores as mentioned above. The rows of figures correspond to the stimulus types in the same order as Table 9 as indicated by the figure labels associated with the figure alphabetic letter. Thus, FIGS. 22A, 22D, 22G present AUC data for the SteadyOld, FIGS. 22B, 22E, 22H are for. FlickNew, and FIGS. 22C, 22F, 22I are for the SteadyNew stimulus. As indicated by the titles, the columns of figures correspond to the three AMD disease severities: mild (FIGS. 22A, 22B, 22C), moderate (FIGS. 22D, 22E, 22F) and severe (FIGS. 22G, 22H, 22I). It is clear from the bottom row of figures, FIGS. 22C, 22F, 22I, that considering any of the first worst to the $7^{th}$ worst deviations from normal provides the FlickNew stimulus type yielded perfect diagnosis, i.e. % AUC of 100% with minimal standard error (as indicted by the error bars being smaller than the data symbols). Apparently the spatially smaller version of the clustered-volley stimuli outperform identically scaled spatially-sparse stimuli, and the pedestal flicker version of the clustered-volley type.

The invention claimed is:

1. A method for assessing the nervous system of a subject, the method comprising the steps of:
   presenting multifocal arrays of stimuli in alternating volleys of individual stimuli selected from at least two stimulus ensembles that are clustered within portions of a sensory field of a subject adapted to evoke pupillary responses from at least one pupil of the subject and where each stimulus ensemble comprises a plurality of individual stimuli, said clustered stimulus ensembles comprising a plurality of individual stimuli drawn from portions of the field surrounding the centre of the sensory field defined within a first inner radius to a second outer radius and from a first polar angle to a second polar angle, selected individual stimuli being concurrently presented according to statistically independent sequences such that on during any time duration that a volley of stimuli are presented from a given cluster such that each individual stimuli has a probability of being presented of about 0.5, the presentation of the stimuli in such volleys overcoming gain control mechanisms that otherwise tend to diminish the responses evoked by the stimuli and thus produce large and more reliable responses from the pupil;
   detecting using a sensor responses of at least one pupil evoked by the stimuli;
   recording and relating the pupillary responses to the function of the subject's neural responses to at least two of the individual stimuli of the clustered stimulus ensembles; and
   determining weight functions for each region of the sensory field tested from the recorded responses of pupil for assessment of the sensory system.

2. The method as claimed in claim 1, wherein the selection of which cluster of stimulus regions is a candidate for display is controlled by a pseudorandom process.

3. The method as claimed in claim 1, wherein the selection of which cluster of stimulus regions is a candidate for display is controlled by a round robin process.

4. The method as claimed in claim 1, wherein the individual stimuli each being controlled by statistically independent stimuli appear a mean presentation interval of between about 1 seconds/region and about 16 seconds/region, and preferably is about 4 seconds/region.

5. The method as claimed in claim 1, wherein the regions that are selected to be within a given clustered stimulus ensemble of stimulus regions are selected so that if an individual region has probability $p_{single}$ of appearing in a given time duration, the probability that any two spatially adjacent neighbouring regions should appear next to each other, $p_{pair}$, is on average across the total array of possible test location less than or equal to $p^2_{single}/2$.

6. The method as claimed in claim 1, wherein both eyes are stimulated concurrently with dichoptic visual stimuli where presentation of each region is controlled by statistically independent sequences, permitting separate weighting function to be estimated.

7. The method as claimed in claim 6, wherein either binocular visual stimuli are used, or where monocular and binocular stimuli are interleaved, so that weighting functions for each can be determined.

8. The method as claimed in claim 1, wherein both pupils are stimulated concurrently so that direct and consensual responses can be estimated for each eye allowing afferent and efferent visual function to be distinguished.

9. The method as claimed in claim 1, wherein the visual stimuli are adapted to provide a measure of the distance to objects in the visual field, by presenting stereo disparity cues to each of the subject's eyes, such that the pupillary responses are representative of the function of the accommodative system of the subject's eyes.

10. The method as claimed in claim 1, wherein the sequence of stimuli is designed to reduce stereoscopic depth cues that occur due to nonlinear interactions that occur over times scales of about 0.5 seconds to minimise spurious accommodative near-responses of the pupils.

11. The method as claimed in claim 1, wherein the recorded measured response is not the time varying pupil diameter but is instead a signal from another part of the accommodative triad, either vergence eye movements or changes in the shape of the lens of the eye, which can be correlated with the pupillary response.

12. The method as claimed in claim 1, wherein: the measured response is not the time varying pupil diameter but is a measure of the pooled neural activity evoked by the clustered stimulus ensemble, and generated from one or more sensory areas in which there is not a well-defined topological map of the sensory space as in the EWN; and a device for recording the evoked responses includes any of detecting electrical or magnetic changes, changes to the absorption, scattering or polarization of infrared light or other electromagnetic radiation from parts of the nervous system, or functional magnetic resonance imaging.

13. The method as claimed in claim 1, wherein borders of said clustered ensembles are arcuate portions defined by horizontal and vertical meridians of the sensory field.

14. The method as claimed in claim 1, wherein the sensory field comprises the visual field of one or both eyes of a subject.

15. The method as claimed in claim 13, wherein the sensory field comprises the visual field of one or both eyes of a subject.

* * * * *